United States Patent [19]
Shiloh et al.

[11] Patent Number: 5,777,093
[45] Date of Patent: Jul. 7, 1998

[54] CDNAS ASSOCIATED WITH ATAXIA-TELANGIECTASIA

[75] Inventors: Yosef Shiloh, Tel Aviv, Israel; Danilo A. Tagle, Gaithersburg; Francis S. Collins, Rockville, both of Md.

[73] Assignee: RAMOT-University Authority for Applied Research & Industrial Development Ltd., Tel Aviv, Israel

[21] Appl. No.: 508,836

[22] Filed: Jul. 28, 1995

Related U.S. Application Data

[63] Continuation-in-part of Ser. No. 493,092, Jun. 21, 1995, which is a continuation-in-part of Ser. No. 441,822, May 16, 1995.

[51] Int. Cl.$^6$ .................................................. C12N 15/00
[52] U.S. Cl. .................. 536/23.5; 536/23.1; 536/23.4; 435/69.1; 435/320.1; 435/325; 435/252.3; 530/350
[58] Field of Search ................... 536/23.5, 23.1, 536/24.1; 530/350; 514/12, 44; 435/320.1, 240.2, 252.3, 252.33, 69.1, 325; 424/93.1

[56] References Cited

U.S. PATENT DOCUMENTS

| | | | |
|---|---|---|---|
| 3,791,932 | 2/1974 | Schuurs et al. | 195/103.5 R |
| 3,839,153 | 10/1974 | Schuurs et al. | 195/103.5 R |
| 3,850,578 | 11/1974 | McConnell | 23/230 B |
| 3,850,752 | 11/1974 | Schuurs et al. | 195/103.5 |
| 3,853,987 | 12/1974 | Dreyer | 424/1 |
| 3,867,517 | 2/1975 | Ling | 424/1 |
| 3,879,262 | 4/1975 | Schuurs et al. | 195/63 |
| 3,901,654 | 8/1975 | Gross | 23/230 B |
| 3,935,074 | 1/1976 | Rubenstein et al. | 195/103.5 R |
| 3,984,533 | 10/1976 | Uzgiris | 424/12 |
| 3,996,345 | 12/1976 | Ullman et al. | 424/12 |
| 4,034,074 | 7/1977 | Miles | 424/1 |
| 4,098,876 | 7/1978 | Piasio et al. | 424/1 |
| 4,736,866 | 4/1988 | Leder et al. | 800/1 |
| 4,879,219 | 11/1989 | Wands et al. | 435/7 |
| 5,011,771 | 4/1991 | Bellet et al. | 435/7.94 |
| 5,175,383 | 12/1992 | Leder et al. | 800/2 |
| 5,175,384 | 12/1992 | Krimpenfort et al. | 800/2 |
| 5,175,385 | 12/1992 | Wagner et al. | 800/2 |
| 5,221,778 | 6/1993 | Bryne et al. | 800/2 |
| 5,281,521 | 1/1994 | Trojanowski et al. | 435/7.5 |
| 5,288,846 | 2/1994 | Quertermous et al. | 435/172.3 |
| 5,298,422 | 3/1994 | Schwartz et al. | 435/320.1 |
| 5,347,075 | 9/1994 | Sorge | 800/2 |
| 5,360,735 | 11/1994 | Weinshank et al. | 435/240.2 |
| 5,387,742 | 2/1995 | Cordell | 800/2 |
| 5,395,767 | 3/1995 | Murnane | 435/320.1 |

FOREIGN PATENT DOCUMENTS

| | | |
|---|---|---|
| WO 9314200 | 7/1993 | WIPO . |
| WO 9400572 | 1/1994 | WIPO . |
| WO 9406908 | 3/1994 | WIPO . |
| WO 9423049 | 10/1994 | WIPO . |
| WO 9428123 | 12/1994 | WIPO . |
| WO 9503431 | 2/1995 | WIPO . |

OTHER PUBLICATIONS

Rasio et al, Cancer Research 55:6053–6057, Dec. 15, 1995.
Kapp, "Cloning of a candidate gene for Ataxia–Telangiectasia Group D" *Am. J. Hum. Genet.*, 51:45–54 (1992).
Leonardt et al., "Nucleotide sequence analysis of a candidate gene for Ataxia–Telangiectasia Group D (ATDC)" *Genomics*, 19:130–136 (1994).
Aksentijevich et al., "Familial mediterranean fever in Moroccan Jews: demonstration of a founder effect by extended haplotype analysis" *Am. J. Hum. Genet.*, 53:644–651 (1993).
Ambrose et al., "A physical map across chromosome 11q22–q23 containing the major locus for ataxia telangiectasia" *Genomics*, 21:612–619 (1994).
Attree et al., "The Lowe's oculocherebronrenal syndrome gene encodes protein highly homologous to inositol polphosphate . . . " *Nature*, 358:239–242 (1992).
Barker, "A more robust, rapid alkaline denaturation sequencing method" *BioTechniques*, vol. 14, No. 2, pp. 168–169 (1993).
Berger et al., "Isolation of a candidate gene for Norrie disease by positional cloning" *Nature Genet.*, 1:199–203, (1992).
Buckler et al., Exon amplification: a strategy to isolate mammalian genes based on RNA splicing *Proc. Natl. Acad. Sci. USA*, 88:4005–4009 (1991).
Burke and Olson, "Preparation of clone libraries in yeast artificial–chromosome vectors" in *Methods in Enzymology*, vol. 194, eds. Guthrie and Fink, Academic Press, Inc., Chap. 17, pp. 251–270 (1991).
Capecchi et al., "Altering the genome by homologous recombination" *Science*, 244:1288–1292 (1989).
Chakravarti et al., "Nonuniform recombination within the human β–globin gene cluster" *Am. J. Hum. Genet.*, 36:1239–1258 (1984).
Chelly et al., "Isolation of a candidate gene for Menkes disease that encodes a potential heavy metal binding protein" *Nature Genet.*, 3:14–19 (1993).
Church et al., "Isolation of genes from complex sources of mammalian genomic DNA using exon amplification" *Nature Genet.*, 6:98–104 (1993).
Collins, "Positional cloning: let's not call it reverse anymore" *Nature Genet.*, 1:3–6 (1992).
Davies et al., "Targeted alterations in yeast artificial chromosomes for inter-species gene transfer" *Nucleic Acids Research*, vol. 20, No. 11, pp. 2693–2698 (1992).
Dickinson et al., "High frequency gene targeting using insertional vectors" *Human Molecular Genetics*, vol. 2, No. 8, pp. 1299–1302 (1993).

(List continued on next page.)

*Primary Examiner*—Stephen Walsh
*Assistant Examiner*—Eliane Lazar-Wesley
*Attorney, Agent, or Firm*—Kohn & Associates

[57] ABSTRACT

A purified and isolated gene, designated ATM, mutations of which cause ataxia-telangiectasia.

15 Claims, 1 Drawing Sheet

OTHER PUBLICATIONS

Duyk et al., "Exon trapping: a genetic screen to identify candidate transcribed sequences in cloned mammalian genomic DNA" *Proc. Natl. Acad. Sci. USA*, 87:8995–8999 (1990).

Foroud et al., "Localization of an ataxia–telangiectasia locus to a 3–cm interval on chromosome 11q23 . . . " *Am. J. Hum. Genet.*, 49:1263–1279 (1991).

Frohman, "On beyond classic RACE (rapid amplification of cDNA ends)" *PCR Methods and Applications*, 4:S40–S58 (1994).

Frohman et al., "Rapid production of full–length cDNAs from rare transcripts: amplification using a single gene–specific . . . " *Proc. Natl. Acad. Sci. USA*, 85:8998–9002 (1988).

Gatti et al., "Genetic haplotyping of ataxia–telangiectasis families localizes the major gene to an 850 kb region . . . " *Int. J. Radiat. Biol.*, vol. 66, No. 6, S57–S62 (1994).

Gatti et al., "Localization of an ataxia–telangiectasia gene to chromosome 11q22–23" *Nature*, 336:577–580 (1988).

Gilboa et al., "Transfer and expression of cloned genes using retroviral vectors" *BioTechniques* 4(6):504–512 (1986).

Hastbacka et al., "Linkage disequilibrium mapping in isolated founder populations: diastrophic dysplasia in Finland" *Nature Genet.*, 2:204–211 (1992).

Hogervorst et al., "Rapid detection of BRCA1 mutations by the protein truncation test" *Nature Genetics*, 10:208–212 (1995).

Huxley et al., "The human HPRT gene on a yeast artificial chromosome is functional when transferred to mouse cells . . . " *Genomics*, 9:742–750 (1991).

Jakobovits et al., "Germ–line transmission and expression of a human–derived yeast artificial chromosome" *Nature*, vol. 362, pp. 255–258 (1993).

James et al., "A radiation hybrid map of 506 STS markers spanning human chromosome 11" *Nature Genet.*, 8:70 (1994).

Kawasaki, ES. "Amplification of RNA", in PCR Protocols: A guide to methods and applications, Innis et al., editors. *Academic Press*, pp. 21–27 (1990).

Kerem et al., "Identification of the cystic fibrosis gene: genetic analysis" *Science*, 245:1073–1080 (1989).

Lamb et al., "Introduction and expression of the 400 kilobase precursor amyloid protein gene in transgenic mice" *Nature Genetics*, vol. 5, pp. 22–29 (1993).

Lange et al., "Localization of an ataxia–telangiectasia gene to a 500 kb interval on chromosome 11q23.1 by linkage analysis . . . " *Am. J. Hum. Genet.*, S7:112–119 (1995).

Lehesjoki et al., "Localization of the EPM1 gene for progressive myoclonus epilepsy on chromosome 21 . . . " *Hum. Mol. Genet.*, 2:1229–1234 (1993).

Lichter et al., "High–resolution mapping of human chromosome 11 by in situ hybridization with cosmid clones" *Science*, 247:64–69 (1990).

Litt and Luty, "A hypervariable microsatellite revealed by in vitro amplification of a dinucleotide repeat within the cardiac muscle" *Am. J. Hum. Genet.*, 44:397–401, (1989).

Llerena et al., "Spontaneous and induced chromosome breakage in chorionic villus samples: a cytogenetic approach . . . " *J. Med. Genet.*, 26:174–178 (1989).

Lovett et al., "Direct selection: A method for the isolation of cDNAs encoded by large genomic regions" *Proc. Natl. Acad. Sci. USA*, 88, pp. 9628–9632 (1991).

McConville et al., "Genetic and physical mapping of the ataxia–telangiectasia locus on chromosome 11q22–q23" *Int. J. Radiat. Biol.*, vol. 66, No. 6, S45–S56 (1994).

McConville et al., "Paired STSs amplified from radiation hybrids, and from associated YACs, identify highly polymorphic loci . . . " *Hum. Mol. Genet.*, 2:969–974 (1993).

McConville et al., "Fine mapping of the chromosome 11q22–23 region using PFGE, linkage and haplotype analysis . . . " *Nucleic Acids Res.*, 18:4335–4343 (1990).

Miki et al., "A strong candidate for the breast and ovarian cancer susceptibility gene BRCA1" *Science*, 266:66–71 (1994).

Mitchison et al., "Fine genetic mapping of the batten disease locus (CLN3) by haplotype analysis . . . " *Genomics*, 16:455–460 (1993).

Morgan et al., "The selective isolation of novel cDNAs encoded by the regions surrounding the human interleukin 4 and 5 genes" *Nucleic Acids Res.*, 20:5173–5179 (1992).

Orita et al., "Detection of polymorphisms of human DNA by gel electrophoresis as single–strand conformation polymorphisms" *Proc. Natl. Acad. Sci. USA*, 86:2766–2770 (1989).

Oskato et al., "Ataxia–telangiectasia: allelic association with 11q22–23 markers in Moroccan–Jewish patients" *43rd Annual Meeting of the American Society of Human Genetics*, New Orleans, LA (1993).

Ozelius et al., "Strong alleleic association between the torsion dystonia gene (DYT1) and loci on chromosome . . . " *Am. J. Hum. Genet.*, 50:619–628 (1992).

Parimoo et al., "cDNA selection: efficient PCR approach for the selection of cDNAs encoded in large chromosomal DNA fragments" *Proc. Natl. Acad. Sci. USA*, 88:9623–9627 (1991).

Pease et al., "Light–generated oligonucleotide arrays for rapid DNA sequence analysis" *Proc. Natl. Acad. Sci. USA*, 91(11):5022–5026 (1994).

Rothstein, "Targeting, disruption, replacement, and allele rescue . . . " in *Methods in Enzymology*, Guthrie and Fink, editors, Academic Press, Inc., Chap. 19, pp. 291–301 (1991).

Rotman et al., "Three dinucleotide repeat polymorphisms at the ataxia–telangiectasia locus" *Human Molecular Genetics*, vol. 3, No. 11, pp. 2079 (1994b).

Rotman et al., "A YAC contig spanning the ataxia–telangiectasia locus (groups A and C) at 11q22–q23" *Genomics*, 24:234–242 (1994c).

Rotman et al., "Physical and genetic mapping at the ATA/ATC locus on chromosome 11q22–23" *Int. J. Radiat. Biol.*, vol. 66, No. 6, S63–S66 (1994d).

Savitsky et al., A single ataxia–telangiectasia gene with a product similar to PI–3 kinase *Science*, 268:1749–1753 (23 Jun. 1995).

Schedl et al., "A yeast artificial chromosome covering the tyrosinase gene confers copy number–dependent expression in transgenic mice" *Nature*, vol. 362, pp. 258–261 (1993).

Sirugo et al., "Friedreich ataxia in Louisiana acadians: demonstration of a founder effect by analysis of microsatellite . . . " *Am. J. Hum. Genet.*, 50:559–566 (1992).

Shiloh, "Ataxia–telangiectasia: closer to unraveling the mystery" *European Journal of Human Genetics*, (1995).

Shiloh et al., "Genetic, physical and functional analysis of the ataxia–telangiectasia locus . . . " *Am. J. Hum. Genet.*, 55 (suppl.), A49 (1994).

Strauss et al., "Germ line transmission of a yeast artificial chromosome spanning the murine $\alpha 1$ (I) collagen locus" *Science*, vol. 259, pp. 1904–1907 (1993).

Tagle et al., "Magnetic bead capture of expressed sequences encoded with large genomic segments" *Nature*, 361:751–753 (1993).

The European Polycystic Kidney Disease Consortium, The polycystic kidney disease 1 gene encodes a 14 kb transcript and lies within a duplicated region on chromosome 16 *Cell*, 77:881–894 (1994).

The Huntington's Disease Collaborative Research Group, "A novel gene containing a trinucleotide repeat that is expanded and unstable on Huntington's disease chromosomes" *Cell*, 72:971–983 (1993).

Trofatter et al., "A novel moesin–, ezrin–, radixin–like gene is a candidate for the neurofibromatosis 2 tumor suppressor" *Cell*, 72:791–800 (1993).

Vanagaite et al., "Physical localization of microsatellite markers at the ataxia–telangiectasia locus at 11q22–q23" *Genomics*, 22:231–233 (1994a).

Vanagaite et al., "A high–density microsatellite map of the ataxia–telangiectasia locus" *Hum. Genet.*, 95:451–454 (1995).

Vetrie et al., "The gene involved in X–linked agammaglobulinaemia is a member of the src family of protein–tyrosine kinases" *Nature*, 361:226–233 (1993).

Wagner et al., "Gene transfer into murine stem cells and mice using retroviral vectors" in *Gene Transfer into Mice*, pp. 691–700.

Weber and May, "Abundant class of human DNA polymorphisms which can by typed using the polymerase chain reaction" *Am. J. Hum. Genet.*, 44:388–396 (1989).

Ziv et al., "Ataxia–telangiectasia: linkage analysis in highly inbred Arab and Druze families and differentiation . . . " *Hum. Genet.*, 88:619–626 (1992).

Ziv et al., "The ATC (ataxia–telangiectasia complementation group C) locus localizes to 11q22–q23" *Genomics*, 9:373–375 (1991).

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 7410 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
CGACAAATGA  GGAATTCAGA  ATTGGTTCCT  TGAGAAATAT  GATGCAGCTA  TGTACACGTT     60

GCTTGAGCAA  CTGTACCAAG  AAGAGTCCAA  ATAAGATTGC  ATCTGGCTTT  TTCCTGCGAT    120

TGTTAACATC  AAAGCTAATG  AATGACATTG  CAGATATTTG  TAAAAGTTTA  GCATCCTTCA    180

TCAAAAAGCC  ATTTGACCGT  GGAGAAGTAG  AATCAATGGA  AGATGATACT  AATGGAAATC    240

TAATGGAGGT  GGAGGATCAG  TCATCCATGA  ATCTATTTAA  CGATTACCCT  GATAGTAGTG    300

TTAGTGATGC  AAACGAACCT  GGAGAGAGCC  AAAGTACCAT  AGGTGCCATT  AATCCTTTAG    360

CTGAAGAATA  TCTGTCAAAG  CAAGATCTAC  TTTTCTTAGA  CATGCTCAAG  TTCTTGTGTT    420

TGTGTGTAAC  TACTGCTCAG  ACCAATACTG  TGTCCTTTAG  GGCAGCTGAT  ATTCGGAGGA    480

AATTGTTAAT  GTTAATTGAT  TCTAGCACGC  TAGAACCTAC  CAAATCCCTC  CACCTGCATA    540

TGTATCTAAT  GCTTTTAAAG  GAGCTTCCTG  GAGAAGAGTA  CCCCTTGCCA  ATGGAAGATG    600
```

```
TTCTTGAACT TCTGAAACCA CTATCCAATG TGTGTTCTTT GTATCGTCGT GACCAAGATG      660
TTTGTAAAAC TATTTTAAAC CATGTCCTTC ATGTAGTGAA AAACCTAGGT CAAAGCAATA      720
TGGACTCTGA GAACACAAGG GATGCTCAAG GACAGTTTCT TACAGTAATT GGAGCATTTT      780
GGCATCTAAC AAAGGAGAGG AAATATATAT TCTCTGTAAG AATGGCCCTA GTAAATTGCC      840
TTAAAACTTT GCTTGAGGCT GATCCTTATT CAAAATGGGC CATTCTTAAT GTAATGGGAA      900
AAGACTTTCC TGTAAATGAA GTATTACAC AATTTCTTGC TGACAATCAT CACCAAGTTC       960
GCATGTTGGC TGCAGAGTCA ATCAATAGAT TGTTCCAGGA CACGAAGGGA GATTCTTCCA     1020
GGTTACTGAA AGCACTTCCT TTGAAGCTTC AGCAAACAGC TTTGAAAAT GCATACTTGA      1080
AAGCTCAGGA AGGAATGAGA GAAATGTCCC ATAGTGCTGA GAACCCTGAA ACTTTGGATG     1140
AAATTTATAA TAGAAAATCT GTTTTACTGA CGTTGATAGC TGTGGTTTTA TCCTGTAGCC     1200
CTATCTGCGA AAAACAGGCT TTGTTGCCC TGTGTAAATC TGTGAAAGAG AATGGATTAG      1260
AACCTCACCT TGTGAAAAAG GTTTTAGAGA AAGTTTCTGA AACTTTTGGA TATAGACGTT     1320
TAGAAGACTT TATGGCATCT CATTTAGATT ATCTGGTTTT GGAATGGCTA AATCTTCAAG     1380
ATACTGAATA CAACTTATCT TCTTTTCCTT TTATTTTATT AAACTACACA ATATTGAGG      1440
ATTTCTATAG ATCTTGTTAT AAGGTTTTGA TTCCACATCT GGTGATTAGA AGTCATTTTG     1500
ATGAGGTGAA GTCCATTGCT AATCAGATTC AAGAGGACTG GAAAAGTCTT CTAACAGACT     1560
GCTTTCCAAA GATTCTTGTA AATATTCTTC CTTATTTTGC CTATGAGGGT ACCAGAGACA     1620
GTGGGATGGC ACAGCAAAGA GAGACTGCTA CCAAGGTCTA TGATATGCTT AAAAGTGAAA     1680
ACTTATTGGG AAAACAGATT GATCACTTAT TCATTAGTAA TTTACCAGAG ATTGTGGTGG     1740
AGTTATTGAT GACGTTACAT GAGCCAGCAA ATTCTAGTGC CAGTCAGAGC ACTGACCTCT     1800
GTGACTTTTC AGGGGATTTG GATCCTGCTC CTAATCCACC TCATTTTCCA TCGCATGTGA     1860
TTAAAGCAAC ATTTGCCTAT ATCAGCAATT GTCATAAAAC CAAGTTAAAA AGCATTTTAG     1920
AAATTCTTTC CAAAAGCCCT GATTCCTATC AGAAAATTCT TCTTGCCATA TGTGAGCAAG     1980
CAGCTGAAAC AAATAATGTT TATAAGAAGC ACAGAATTCT TAAAATATAT CACCTGTTTG     2040
TTAGTTTATT ACTGAAAGAT ATAAAAAGTG GCTTAGGAGG AGCTTGGGCC TTTGTTCTTC     2100
GAGACGTTAT TTATACTTTG ATTCACTATA TCAACCAAAG GCCTTCTTGT ATCATGGATG     2160
TGTCATTACG TAGCTTCTCC CTTTGTTGTG ACTTATTAAG TCAGGTTTGC CAGACAGCCG     2220
TGACTTACTG TAAGGATGCT CTAGAAAACC ATCTTCATGT TATTGTTGGT ACACTTATAC     2280
CCCTTGTGTA TGAGCAGGTG GAGGTTCAGA AACAGGTATT GGACTTGTTG AAATACTTAG     2340
TGATAGATAA CAAGGATAAT GAAAACCTCT ATATCACGAT TAAGCTTTTA GATCCTTTTC     2400
CTGACCATGT TGTTTTAAG GATTTGCGTA TTACTCAGCA AAAAATCAAA TACAGTAGAG      2460
GACCCTTTTC ACTCTTGGAG GAAATTAACC ATTTTCTCTC AGTAAGTGTT TATGATGCAC     2520
TTCCATTGAC AAGACTTGAA GGACTAAAGG ATCTTCGAAG ACAACTGGAA CTACATAAAG     2580
ATCAGATGGT GGACATTATG AGAGCTTCTC AGGATAATCC GCAAGATGGG ATTATGGTGA     2640
AACTAGTTGT CAATTTGTTG CAGTTATCCA AGATGGCAAT AAACCACACT GGTGAAAAAG     2700
AAGTTCTAGA GGCTGTTGGA AGCTGCTTGG GAGAAGTGGG TCCTATAGAT TTCTCTACCA     2760
TAGCTATACA ACATAGTAAA GATGCATCTT ATACCAAGGC CCTTAAGTTA TTTGAAGATA     2820
AAGAACTTCA GTGGACCTTC ATAATGCTGA CCTACCTGAA TAACACACTG GTAGAAGATT     2880
GTGTCAAAGT TCGATCAGCA GCTGTTACCT GTTTGAAAAA CATTTTAGCC ACAAAGACTG     2940
GACATAGTTT CTGGGAGATT TATAAGATGA CAACAGATCC AATGCTGGCC TATCTACAGC     3000
```

```
CTTTTAGAAC ATCAAGAAAA AAGTTTTTAG AAGTACCCAG ATTTGACAAA GAAAACCCTT    3060
TTGAAGGCCT GGATGATATA AATCTGTGGA TTCCTCTAAG TGAAAATCAT GACATTTGGA    3120
TAAAGACACT GACTTGTGCT TTTTGGACA  GTGGAGGCAC AAAATGTGAA ATTCTTCAAT    3180
TATTAAAGCC AATGTGTGAA GTGAAAACTG ACTTTGTCA  GACTGTACTT CCATACTTGA    3240
TTCATGATAT TTTACTCCAA GATACAAATG AATCATGGAG AAATCTGCTT TCTACACATG    3300
TTCAGGGATT TTTCACCAGC TGTCTTCGAC ACTTCTCGCA AACGAGCCGA TCCACAACCC    3360
CTGCAAACTT GGATTCAGAG TCAGAGCACT TTTTCCGATG CTGTTTGGAT AAAAAATCAC    3420
AAAGAACAAT GCTTGCTGTT GTGGACTACA TGAGAAGACA AAAGAGACCT TCTTCAGGAA    3480
CAATTTTTAA TGATGCTTTC TGGCTGGATT TAAATTATCT AGAAGTTGCC AAGGTAGCTC    3540
AGTCTTGTGC TGCTCACTTT ACAGCTTTAC TCTATGCAGA AATCTATGCA GATAAGAAAA    3600
GTATGGATGA TCAAGAGAAA AGAAGTCTTG CATTTGAAGA AGGAAGCCAG AGTACAACTA    3660
TTTCTAGCTT GAGTGAAAAA AGTAAAGAAG AAACTGGAAT AAGTTTACAG GATCTTCTCT    3720
TAGAAATCTA CAGAAGTATA GGGGAGCCAG ATAGTTTGTA TGGCTGTGGT GGAGGGAAGA    3780
TGTTACAACC CATTACTAGA CTACGAACAT ATGAACACGA AGCAATGTGG GGCAAAGCCC    3840
TAGTAACATA TGACCTCGAA ACAGCAATCC CCTCATCAAC ACGCCAGGCA GGAATCATTC    3900
AGGCCTTGCA GAATTTGGGA CTCTGCCATA TTCTTTCCGT CTATTTAAAA GGATTGGATT    3960
ATGAAAATAA AGACTGGTGT CCTGAACTAG AAGAACTTCA TTACCAAGCA GCATGGAGGA    4020
ATATGCAGTG GGACCATTGC ACTTCCGTCA GCAAAGAAGT AGAAGGAACC AGTTACCATG    4080
AATCATTGTA CAATGCTCTA CAATCTCTAA GAGACAGAGA ATTCTCTACA TTTTATGAAA    4140
GTCTCAAATA TGCCAGAGTA AAAGAAGTGG AAGAGATGTG TAAGCGCAGC CTTGAGTCTG    4200
TGTATTCGCT CTATCCCACA CTTAGCAGGT TGCAGGCCAT TGGAGAGCTG GAAAGCATTG    4260
GGGAGCTTTT CTCAAGATCA GTCACACATA GACAACTCTC TGAAGTATAT ATTAAGTGGC    4320
AGAAACACTC CCAGCTTCTC AAGGACAGTG ATTTTAGTTT TCAGGAGCCT ATCATGGCTC    4380
TACGCACAGT CATTTTGGAG ATCCTGATGG AAAAGGAAAT GGACAACTCA CAAAGAGAAT    4440
GTATTAAGGA CATTCTCACC AAACACCTTG TAGAACTCTC TATACTGGCC AGAACTTTCA    4500
AGAACACTCA GCTCCCTGAA AGGGCAATAT TTCAAATTAA ACAGTACAAT TCAGTTAGCT    4560
GTGGAGTCTC TGAGTGGCAG CTGGAAGAAG CACAAGTATT CTGGGCAAAA AAGGAGCAGA    4620
GTCTTGCCCT GAGTATTCTC AAGCAAATGA TCAAGAAGTT GGATGCCAGC TGTGCAGCGA    4680
ACAATCCCAG CCTAAAACTT ACATACACAG AATGTCTGAG GGTTTGTGGC AACTGGTTAG    4740
CAGAAACGTG CTTAGAAAAT CCTGCGGTCA TCATGCAGAC CTATCTAGAA AAGGCAGTAG    4800
AAGTTGCTGG AAATTATGAT GGAGAAAGTA GTGATGAGCT AAGAAATGGA AAAATGAAGG    4860
CATTTCTCTC ATTAGCCCGG TTTTCAGATA CTCAATACCA AGAATTGAA  AACTACATGA    4920
AATCATCGGA ATTTGAAAAC AAGCAAGCTC TCCTGAAAAG AGCCAAAGAG GAAGTAGGTC    4980
TCCTTAGGGA ACATAAAATT CAGACAAACA GATACACAGT AAAGGTTCAG CGAGAGCTGG    5040
AGTTGGATGA ATTAGCCCTG CGTGCACTGA AAGAGGATCG TAAACGCTTC TTATGTAAAG    5100
CAGTTGAAAA TTATATCAAC TGCTTATTAA GTGGAGAAGA ACATGATATG TGGGTATTCC    5160
GGCTTTGTTC CCTCTGGCTT GAAAATTCTG GAGTTTCTGA AGTCAATGGC ATGATGAAGA    5220
GAGACGGAAT GAAGATTCCA ACATATAAAT TTTGCCTCT  TATGTACCAA TTGGCTGCTA    5280
GAATGGGGAC CAAGATGATG GGAGGCCTAG GATTTCATGA AGTCCTCAAT AATCTAATCT    5340
CTAGAATTTC AATGGATCAC CCCCATCACA CTTTGTTTAT TATACTGGCC TTAGCAAATG    5400
```

```
CAAACAGAGA TGAATTTCTG ACTAAACCAG AGGTAGCCAG AAGAAGCAGA ATAACTAAAA    5460
ATGTGCCTAA ACAAAGCTCT CAGCTTGATG AGGATCGAAC AGAGGCTGCA AATAGAATAA    5520
TATGTACTAT CAGAAGTAGG AGACCTCAGA TGGTCAGAAG TGTTGAGGCA CTTTGTGATG    5580
CTTATATTAT ATTAGCAAAC TTAGATGCCA CTCAGTGGAA GACTCAGAGA AAAGGCATAA    5640
ATATTCCAGC AGACCAGCCA ATTACTAAAC TTAAGAATTT AGAAGATGTT GTTGTCCCTA    5700
CTATGGAAAT TAAGGTGGAC CACACAGGAG AATATGGAAA TCTGGTGACT ATACAGTCAT    5760
TTAAAGCAGA ATTTCGCTTA GCAGGAGGTG TAAATTTACC AAAAATAATA GATTGTGTAG    5820
GTTCCGATGG CAAGGAGAGG AGACAGCTTG TTAAGGGCCG TGATGACCTG AGACAAGATG    5880
CTGTCATGCA ACAGGTCTTC CAGATGTGTA ATACATTACT GCAGAGAAAC ACGGAAACTA    5940
GGAAGAGGAA ATTAACTATC TGTACTTATA AGGTGGTTCC CCTCTCTCAG CGAAGTGGTG    6000
TTCTTGAATG GTGCACAGGA ACTGTCCCCA TTGGTGAATT TCTTGTTAAC AATGAAGATG    6060
GTGCTCATAA AAGATACAGG CCAAATGATT TCAGTGCCTT TCAGTGCCAA AAGAAAATGA    6120
TGGAGGTGCA AAAAAGTCT  TTTGAAGAGA AATATGAAGT CTTCATGGAT GTTTGCCAAA    6180
ATTTTCAACC AGTTTTCCGT TACTTCTGCA TGGAAAAATT CTTGGATCCA GCTATTTGGT    6240
TTGAGAAGCG ATTGGCTTAT ACGCGCAGTG TAGCTACTTC TTCTATTGTT GGTTACATAC    6300
TTGGACTTGG TGATAGACAT GTACAGAATA TCTTGATAAA TGAGCAGTCA GCAGAACTTG    6360
TACATATAGA TCTAGGTGTT GCTTTTGAAC AGGGCAAAAT CCTTCCTACT CCTGAGACAG    6420
TTCCTTTTAG ACTCACCAGA GATATTGTGG ATGGCATGGG CATTACGGGT GTTGAAGGTG    6480
TCTTCAGAAG ATGCTGTGAG AAAACCATGG AAGTGATGAG AAACTCTCAG GAAACTCTGT    6540
TAACCATTGT AGAGGTCCTT CTATATGATC CACTCTTTGA CTGGACCATG AATCCTTTGA    6600
AAGCTTTGTA TTTACAGCAG AGGCCGGAAG ATGAAACTGA GCTTCACCCT ACTCTGAATG    6660
CAGATGACCA AGAATGCAAA CGAAATCTCA GTGATATTGA CCAGAGTTTC GACAAAGTAG    6720
CTGAACGTGT CTTAATGAGA CTACAAGAGA AACTGAAAGG AGTGGAAGAA GGCACTGTGC    6780
TCAGTGTTGG TGGACAGGTG AAATTGCTCA TACAGCAGGC CATAGACCCC AAAAATCTCA    6840
GCCGACTTTT CCCAGGATGG AAAGCTTGGG TGTGATCTTC AGTATATGAA TTACCCTTTC    6900
ATTCAGCCTT TAGAAATTAT ATTTTAGCCT TTATTTTTAA CCTGCCAACA TACTTTAAGT    6960
AGGGATTAAT ATTTAAGTGA ACTATTGTGG GTTTTTTTGA ATGTTGGTTT TAATACTTGA    7020
TTTAATCACC ACTCAAAAAT GTTTTGATGG TCTTAAGGAA CATCTCTGCT TTCACTCTTT    7080
AGAAATAATG GTCATTCGGG CTGGGCGCAG CGGCTCACGC CTGTAATCCC AGCACTTTGG    7140
GAGGCCGAGG TGAGCGGATC ACAAGGTCAG GAGTTCGAGA CCAGCCTGGC CAAGAGACCA    7200
GCCTGGCCAG TATGGTGAAA CCCTGTCTCT ACTAAAAATA CAAAAATTAG CCGAGCATGG    7260
TGGCGGGCAC CTGTAGTCCC AGCTACTCGA GAGGCTGAGG CAGGAGAATC TCTTGAACCT    7320
GGGAGGTGAA GGTTGCTGTG GGCCAAAATC ATGCCATTGC ACTCCAGCCT GGGTGACAAG    7380
AGCGAAACTC CATCTCAAAA AWWAAAAAAA                                    7410
```

( 2 ) INFORMATION FOR SEQ ID NO:2:

( i ) SEQUENCE CHARACTERISTICS:
        ( A ) LENGTH: 1708 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

-continued

| | | | | | | | | | | | | | | |
|---|---|---|---|---|---|---|---|---|---|---|---|---|---|---|
|Met 1|Thr|Leu|His|Glu 5|Pro|Ala|Asn|Ser|Ser 10|Ala|Ser|Gln|Ser|Thr 15|Asp|
|Leu|Cys|Asp|Phe 20|Ser|Gly|Asp|Leu|Asp 25|Pro|Ala|Pro|Asn|Pro 30|Pro|His|
|Phe|Pro|Ser 35|His|Val|Ile|Lys|Ala 40|Thr|Phe|Ala|Tyr|Ile 45|Ser|Asn|Cys|
|His|Lys 50|Thr|Lys|Leu|Lys|Ser 55|Ile|Leu|Glu|Ile|Leu 60|Ser|Lys|Ser|Pro|
|Asp 65|Ser|Tyr|Gln|Lys|Ile 70|Leu|Leu|Ala|Ile|Cys 75|Glu|Gln|Ala|Ala|Glu 80|
|Thr|Asn|Asn|Val|Tyr 85|Lys|Lys|His|Arg|Ile 90|Leu|Lys|Ile|Tyr|His 95|Leu|
|Phe|Val|Ser|Leu 100|Leu|Leu|Lys|Asp|Ile 105|Lys|Ser|Gly|Leu|Gly 110|Gly|Ala|
|Trp|Ala|Phe 115|Val|Leu|Arg|Asp|Val 120|Ile|Tyr|Thr|Leu|Ile 125|His|Tyr|Ile|
|Asn|Gln 130|Arg|Pro|Ser|Cys|Ile 135|Met|Asp|Val|Ser|Leu 140|Arg|Ser|Phe|Ser|
|Leu 145|Cys|Cys|Asp|Leu|Leu 150|Ser|Gln|Val|Cys|Gln 155|Thr|Ala|Val|Thr|Tyr 160|
|Cys|Lys|Asp|Ala|Leu 165|Glu|Asn|His|Leu|His 170|Val|Ile|Val|Gly|Thr 175|Leu|
|Ile|Pro|Leu|Val 180|Tyr|Glu|Gln|Val|Glu 185|Val|Gln|Lys|Gln|Val 190|Leu|Asp|
|Leu|Leu|Lys 195|Tyr|Leu|Val|Ile|Asp 200|Asn|Lys|Asp|Asn|Glu 205|Asn|Leu|Tyr|
|Ile|Thr 210|Ile|Lys|Leu|Leu|Asp 215|Pro|Phe|Pro|Asp|His 220|Val|Val|Phe|Lys|
|Asp 225|Leu|Arg|Ile|Thr|Gln 230|Gln|Lys|Ile|Lys|Tyr 235|Ser|Arg|Gly|Pro|Phe 240|
|Ser|Leu|Leu|Glu|Glu 245|Ile|Asn|His|Phe|Leu 250|Ser|Val|Ser|Val|Tyr 255|Asp|
|Ala|Leu|Pro|Leu 260|Thr|Arg|Leu|Glu|Gly 265|Leu|Lys|Asp|Leu|Arg 270|Arg|Gln|
|Leu|Glu|Leu 275|His|Lys|Asp|Gln|Met 280|Val|Asp|Ile|Met|Arg 285|Ala|Ser|Gln|
|Asp|Asn 290|Pro|Gln|Asp|Gly|Ile 295|Met|Val|Lys|Leu|Val 300|Val|Asn|Leu|Leu|
|Gln 305|Leu|Ser|Lys|Met|Ala 310|Ile|Asn|His|Thr|Gly 315|Glu|Lys|Glu|Val|Leu 320|
|Glu|Ala|Val|Gly|Ser 325|Cys|Leu|Gly|Glu|Val 330|Gly|Pro|Ile|Asp|Phe 335|Ser|
|Thr|Ile|Ala|Ile 340|Gln|His|Ser|Lys|Asp 345|Ala|Ser|Tyr|Thr|Lys 350|Ala|Leu|
|Lys|Leu|Phe 355|Glu|Asp|Lys|Glu|Leu 360|Gln|Trp|Thr|Phe|Ile 365|Met|Leu|Thr|
|Tyr|Leu 370|Asn|Asn|Thr|Leu|Val 375|Glu|Asp|Cys|Val|Lys 380|Val|Arg|Ser|Ala|
|Ala 385|Val|Thr|Cys|Leu|Lys 390|Asn|Ile|Leu|Ala|Thr 395|Lys|Thr|Gly|His|Ser 400|
|Phe|Trp|Glu|Ile|Tyr 405|Lys|Met|Thr|Thr|Asp 410|Pro|Met|Leu|Ala|Tyr 415|Leu|
|Gln|Pro|Phe|Arg 420|Thr|Ser|Arg|Lys|Lys 425|Phe|Leu|Glu|Val|Pro 430|Arg|Phe|

-continued

| | | | | | | | | | | | | |
|---|---|---|---|---|---|---|---|---|---|---|---|---|
| Asp | Lys | Glu | Asn | Pro | Phe | Glu | Gly | Leu | Asp | Asp | Ile | Asn | Leu | Trp | Ile |
| | | 435 | | | | 440 | | | | 445 | | | |
| Pro | Leu | Ser | Glu | Asn | His | Asp | Ile | Trp | Ile | Lys | Thr | Leu | Thr | Cys | Ala |
| | 450 | | | | | 455 | | | | 460 | | | |
| Phe | Leu | Asp | Ser | Gly | Gly | Thr | Lys | Cys | Glu | Ile | Leu | Gln | Leu | Leu | Lys |
| 465 | | | | | 470 | | | | 475 | | | | 480 |
| Pro | Met | Cys | Glu | Val | Lys | Thr | Asp | Phe | Cys | Gln | Thr | Val | Leu | Pro | Tyr |
| | | | | 485 | | | | | 490 | | | | | 495 |
| Leu | Ile | His | Asp | Ile | Leu | Leu | Gln | Asp | Thr | Asn | Glu | Ser | Trp | Arg | Asn |
| | | | 500 | | | | 505 | | | | | 510 | |
| Leu | Leu | Ser | Thr | His | Val | Gln | Gly | Phe | Phe | Thr | Ser | Cys | Leu | Arg | His |
| | | 515 | | | | 520 | | | | | 525 | | |
| Phe | Ser | Gln | Thr | Ser | Arg | Ser | Thr | Thr | Pro | Ala | Asn | Leu | Asp | Ser | Glu |
| | | 530 | | | | 535 | | | | 540 | | | |
| Ser | Glu | His | Phe | Phe | Arg | Cys | Cys | Leu | Asp | Lys | Lys | Ser | Gln | Arg | Thr |
| 545 | | | | | 550 | | | | 555 | | | | 560 |
| Met | Leu | Ala | Val | Val | Asp | Tyr | Met | Arg | Arg | Gln | Lys | Arg | Pro | Ser | Ser |
| | | | | 565 | | | | 570 | | | | | 575 |
| Gly | Thr | Ile | Phe | Asn | Asp | Ala | Phe | Trp | Leu | Asp | Leu | Asn | Tyr | Leu | Glu |
| | | | 580 | | | | 585 | | | | | 590 | |
| Val | Ala | Lys | Val | Ala | Gln | Ser | Cys | Ala | Ala | His | Phe | Thr | Ala | Leu | Leu |
| | | 595 | | | | 600 | | | | 605 | | | |
| Tyr | Ala | Glu | Ile | Tyr | Ala | Asp | Lys | Lys | Ser | Met | Asp | Asp | Gln | Glu | Lys |
| | 610 | | | | | 615 | | | | 620 | | | |
| Arg | Ser | Leu | Ala | Phe | Glu | Glu | Gly | Ser | Gln | Ser | Thr | Thr | Ile | Ser | Ser |
| 625 | | | | | 630 | | | | 635 | | | | 640 |
| Leu | Ser | Glu | Lys | Ser | Lys | Glu | Glu | Thr | Gly | Ile | Ser | Leu | Gln | Asp | Leu |
| | | | | 645 | | | | 650 | | | | | 655 |
| Leu | Leu | Glu | Ile | Tyr | Arg | Ser | Ile | Gly | Glu | Pro | Asp | Ser | Leu | Tyr | Gly |
| | | | 660 | | | | 665 | | | | | 670 | |
| Cys | Gly | Gly | Gly | Lys | Met | Leu | Gln | Pro | Ile | Thr | Arg | Leu | Arg | Thr | Tyr |
| | | 675 | | | | 680 | | | | 685 | | | |
| Glu | His | Glu | Ala | Met | Trp | Gly | Lys | Ala | Leu | Val | Thr | Tyr | Asp | Leu | Glu |
| | 690 | | | | | 695 | | | | 700 | | | |
| Thr | Ala | Ile | Pro | Ser | Ser | Thr | Arg | Gln | Ala | Gly | Ile | Ile | Gln | Ala | Leu |
| 705 | | | | | 710 | | | | 715 | | | | 720 |
| Gln | Asn | Leu | Gly | Leu | Cys | His | Ile | Leu | Ser | Val | Tyr | Leu | Lys | Gly | Leu |
| | | | | 725 | | | | 730 | | | | | 735 |
| Asp | Tyr | Glu | Asn | Lys | Asp | Trp | Cys | Pro | Glu | Leu | Glu | Glu | Leu | His | Tyr |
| | | | 740 | | | | 745 | | | | | 750 | |
| Gln | Ala | Ala | Trp | Arg | Asn | Met | Gln | Trp | Asp | His | Cys | Thr | Ser | Val | Ser |
| | | 755 | | | | 760 | | | | 765 | | | |
| Lys | Glu | Val | Glu | Gly | Thr | Ser | Tyr | His | Glu | Ser | Leu | Tyr | Asn | Ala | Leu |
| | 770 | | | | | 775 | | | | 780 | | | |
| Gln | Ser | Leu | Arg | Asp | Arg | Glu | Phe | Ser | Thr | Phe | Tyr | Glu | Ser | Leu | Lys |
| 785 | | | | | 790 | | | | 795 | | | | 800 |
| Tyr | Ala | Arg | Val | Lys | Glu | Val | Glu | Glu | Met | Cys | Lys | Arg | Ser | Leu | Glu |
| | | | | 805 | | | | 810 | | | | | 815 |
| Ser | Val | Tyr | Ser | Leu | Tyr | Pro | Thr | Leu | Ser | Arg | Leu | Gln | Ala | Ile | Gly |
| | | | 820 | | | | 825 | | | | | 830 | |
| Glu | Leu | Glu | Ser | Ile | Gly | Glu | Leu | Phe | Ser | Arg | Ser | Val | Thr | His | Arg |
| | | 835 | | | | 840 | | | | 845 | | | |
| Gln | Leu | Ser | Glu | Val | Tyr | Ile | Lys | Trp | Gln | Lys | His | Ser | Gln | Leu | Leu |

-continued

|   |   |   | 850 |   |   |   |   |   | 855 |   |   |   |   | 860 |   |
|---|---|---|---|---|---|---|---|---|---|---|---|---|---|---|---|

Lys Asp Ser Asp Phe Ser Phe Gln Glu Pro Ile Met Ala Leu Arg Thr
865                 870             875                 880

Val Ile Leu Glu Ile Leu Met Glu Lys Glu Met Asp Asn Ser Gln Arg
                885             890                 895

Glu Cys Ile Lys Asp Ile Leu Thr Lys His Leu Val Glu Leu Ser Ile
            900             905             910

Leu Ala Arg Thr Phe Lys Asn Thr Gln Leu Pro Glu Arg Ala Ile Phe
        915             920             925

Gln Ile Lys Gln Tyr Asn Ser Val Ser Cys Gly Val Ser Glu Trp Gln
930             935             940

Leu Glu Glu Ala Gln Val Phe Trp Ala Lys Lys Glu Gln Ser Leu Ala
945             950             955             960

Ser Leu Ile Leu Lys Gln Met Ile Lys Lys Leu Asp Ala Ser Cys Ala
            965             970             975

Ala Asn Asn Pro Ser Leu Lys Leu Thr Tyr Thr Glu Cys Leu Arg Val
            980             985             990

Cys Gly Asn Trp Leu Ala Glu Thr Cys Leu Glu Asn Pro Ala Val Ile
            995             1000            1005

Met Gln Thr Tyr Leu Glu Lys Ala Val Glu Val Ala Gly Asn Tyr Asp
            1010            1015            1020

Gly Glu Ser Ser Asp Glu Leu Arg Asn Gly Lys Met Lys Ala Phe Leu
1025            1030            1035            1040

Ser Leu Ala Arg Phe Ser Asp Thr Gln Tyr Gln Arg Ile Glu Asn Tyr
            1045            1050            1055

Met Lys Ser Ser Glu Phe Glu Asn Lys Gln Ala Leu Leu Lys Arg Ala
            1060            1065            1070

Lys Glu Glu Val Gly Leu Leu Arg Glu His Lys Ile Gln Thr Asn Arg
            1075            1080            1085

Tyr Thr Val Lys Val Gln Arg Glu Leu Glu Leu Asp Glu Leu Ala Leu
            1090            1095            1100

Arg Ala Leu Lys Glu Asp Arg Lys Arg Phe Leu Cys Lys Ala Val Glu
1105            1110            1115            1120

Asn Tyr Ile Asn Cys Leu Leu Ser Gly Glu Glu His Asp Met Trp Val
            1125            1130            1135

Phe Arg Leu Cys Ser Leu Trp Leu Glu Asn Ser Gly Val Ser Glu Val
            1140            1145            1150

Asn Gly Met Met Lys Arg Asp Gly Met Lys Ile Pro Thr Tyr Lys Phe
            1155            1160            1165

Leu Pro Leu Met Tyr Gln Leu Ala Ala Arg Met Gly Thr Lys Met Met
            1170            1175            1180

Gly Gly Leu Gly Phe His Glu Val Leu Asn Asn Leu Ile Ser Arg Ile
1185            1190            1195            1200

Ser Met Asp His Pro His His Thr Leu Phe Ile Ile Leu Ala Leu Ala
            1205            1210            1215

Asn Ala Asn Arg Asp Glu Phe Leu Thr Lys Pro Glu Val Ala Arg Arg
            1220            1225            1230

Ser Arg Ile Thr Lys Asn Val Pro Lys Gln Ser Ser Gln Leu Asp Glu
            1235            1240            1245

Asp Arg Thr Glu Ala Ala Asn Arg Ile Ile Cys Thr Ile Arg Ser Arg
            1250            1255            1260

Arg Pro Gln Met Val Arg Ser Val Glu Ala Leu Cys Asp Ala Tyr Ile
1265            1270            1275            1280

```
Ile Leu Ala Asn Leu Asp Ala Thr Gln Trp Lys Thr Gln Arg Lys Gly
            1285                    1290                1295
Ile Asn Ile Pro Ala Asp Gln Pro Ile Thr Lys Leu Lys Asn Leu Glu
            1300                    1305                1310
Asp Val Val Val Pro Thr Met Glu Ile Lys Val Asp His Thr Gly Glu
            1315                    1320                1325
Tyr Gly Asn Leu Val Thr Ile Gln Ser Phe Lys Ala Glu Phe Arg Leu
            1330                    1335                1340
Ala Gly Gly Val Asn Leu Pro Lys Ile Ile Asp Cys Val Gly Ser Asp
1345                    1350                    1355                1360
Gly Lys Glu Arg Arg Gln Leu Val Lys Gly Arg Asp Asp Leu Arg Gln
                1365                    1370                1375
Asp Ala Val Met Gln Gln Val Phe Gln Met Cys Asn Thr Leu Leu Gln
                1380                    1385                1390
Arg Asn Thr Glu Thr Arg Lys Arg Lys Leu Thr Ile Cys Thr Tyr Lys
                1395                    1400                1405
Val Val Pro Leu Ser Gln Arg Ser Gly Val Leu Glu Trp Cys Thr Gly
            1410                    1415                1420
Thr Val Pro Ile Gly Glu Phe Leu Val Asn Asn Glu Asp Gly Ala His
1425                    1430                    1435                1440
Lys Arg Tyr Arg Pro Asn Asp Phe Ser Ala Phe Gln Cys Gln Lys Lys
                1445                    1450                1455
Met Met Glu Val Gln Lys Lys Ser Phe Glu Glu Lys Tyr Glu Val Phe
                1460                    1465                1470
Met Asp Val Cys Gln Asn Phe Gln Pro Val Phe Arg Tyr Phe Cys Met
            1475                    1480                1485
Glu Lys Phe Leu Asp Pro Ala Ile Trp Phe Glu Lys Arg Leu Ala Tyr
            1490                    1495                1500
Thr Arg Ser Val Ala Thr Ser Ser Ile Val Gly Tyr Ile Leu Gly Leu
1505                    1510                    1515                1520
Gly Asp Arg His Val Gln Asn Ile Leu Ile Asn Glu Gln Ser Ala Glu
                1525                    1530                1535
Leu Val His Ile Asp Leu Gly Val Ala Phe Glu Gln Gly Lys Ile Leu
            1540                    1545                1550
Pro Thr Pro Glu Thr Val Pro Phe Arg Leu Thr Arg Asp Ile Val Asp
            1555                    1560                1565
Gly Met Gly Ile Thr Gly Val Glu Gly Val Phe Arg Arg Cys Cys Glu
            1570                    1575                1580
Lys Thr Met Glu Val Met Arg Asn Ser Gln Glu Thr Leu Leu Thr Ile
1585                    1590                    1595                1600
Val Glu Val Leu Leu Tyr Asp Pro Leu Phe Asp Trp Thr Met Asn Pro
            1605                    1610                1615
Leu Lys Ala Leu Tyr Leu Gln Gln Arg Pro Glu Asp Glu Thr Glu Leu
            1620                    1625                1630
His Pro Thr Leu Asn Ala Asp Asp Gln Glu Cys Lys Arg Asn Leu Ser
            1635                    1640                1645
Asp Ile Asp Gln Ser Phe Asp Lys Val Ala Glu Arg Val Leu Met Arg
            1650                    1655                1660
Leu Gln Glu Lys Leu Lys Gly Val Glu Glu Gly Thr Val Leu Ser Val
1665                    1670                    1675                1680
Gly Gly Gln Val Asn Leu Leu Ile Gln Gln Ala Ile Asp Pro Lys Asn
                1685                    1690                1695
Leu Ser Arg Leu Phe Pro Gly Trp Lys Ala Trp Val
            1700                    1705
```

( 2 ) INFORMATION FOR SEQ ID NO:3:

( i ) SEQUENCE CHARACTERISTICS:
    ( A ) LENGTH: 6525 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:3:

| | | | | | |
|---|---|---|---|---|---|
| ATATTGAGGA | TTTCTATAGA | TCTTGTTATA | AGGTTTTGAT | TCCACATCTG | GTGATTAGAA | 60 |
| GTCATTTTGA | TGAGGTGAAG | TCCATTGCTA | ATCAGATTCA | AGAGGACTGG | AAAAGTCTTC | 120 |
| TAACAGACTG | CTTTCCAAAG | ATTCTTGTAA | ATATTCTTCC | TTATTTTGCC | TATGAGGGTA | 180 |
| CCAGAGACAG | TGGGATGGCA | CAGCAAAGAG | AGACTGCTAC | CAAGGTCTAT | GATATGCTTA | 240 |
| AAAGTGAAAA | CTTATTGGGA | AACAGTCTA | CAGGTTGGCT | GCATAGAAGA | AAAAGGTAGA | 300 |
| GTTATTTATA | ATCTTGTAAA | TCTTGGACTT | TGAGTCATCT | ATTTCTTTT | ACAGTCATCG | 360 |
| AATACTTTTG | GAAATAAGAT | TGATCACTTA | TTCATTAGTA | ATTACCAGA | GATTGTGGTG | 420 |
| GAGTTATTGA | TGACGTTACA | TGAGCCAGCA | AATTCTAGTG | CCAGTCAGAG | CACTGACCTC | 480 |
| TGTGACTTTT | CAGGGGATTT | GGATCCTGCT | CCTAATCCAC | CTCATTTTCC | ATCGCATGTG | 540 |
| ATTAAAGCAA | CATTTGCCTA | TATCAGCAAT | TGTCATAAAA | CCAAGTTAAA | AAGCATTTTA | 600 |
| GAAATTCTTT | CCAAAAGCCC | TGATTCCTAT | CAGAAAATTC | TTCTTGCCAT | ATGTGAGCAA | 660 |
| GCAGCTGAAA | CAAATAATGT | TTATAAGAAG | CACAGAATTC | TTAAAATATA | TCACCTGTTT | 720 |
| GTTAGTTTAT | TACTGAAAGA | TATAAAAAGT | GGCTTAGGAG | GAGCTTGGGC | CTTTGTTCTT | 780 |
| CGAGACGTTA | TTTATACTTT | GATTCACTAT | ATCAACCAAA | GGCCTTCTTG | TATCATGGAT | 840 |
| GTGTCATTAC | GTAGCTTCTC | CCTTTGTTGT | GACTTATTAA | GTCAGGTTTG | CCAGACAGCC | 900 |
| GTGACTTACT | GTAAGGATGC | TCTAGAAAAC | CATCTTCATG | TTATTGTTGG | TACACTTATA | 960 |
| CCCCTTGTGT | ATGAGCAGGT | GGAGGTTCAG | AAACAGGTAT | TGGACTTGTT | GAAATACTTA | 1020 |
| GTGATAGATA | ACAAGGATAA | TGAAAACCTC | TATATCACGA | TTAAGCTTTT | AGATCCTTTT | 1080 |
| CCTGACCATG | TTGTTTTTAA | GGATTTGCGT | ATTACTCAGC | AAAAAATCAA | ATACAGTAGA | 1140 |
| GGACCCTTTT | CACTCTTGGA | GGAAATTAAC | CATTTCTCT | CAGTAAGTGT | TTATGATGCA | 1200 |
| CTTCCATTGA | CAAGACTTGA | AGGACTAAAG | GATCTTCGAA | GACAACTGGA | ACTACATAAA | 1260 |
| GATCAGATGG | TGGACATTAT | GAGAGCTTCT | CAGGATAATC | CGCAAGATGG | GATTATGGTG | 1320 |
| AAACTAGTTG | TCAATTTGTT | GCAGTTATCC | AAGATGGCAA | TAAACCACAC | TGGTGAAAAA | 1380 |
| GAAGTTCTAG | AGGCTGTTGG | AAGCTGCTTG | GGAGAAGTGG | GTCCTATAGA | TTTCTCTACC | 1440 |
| ATAGCTATAC | AACATAGTAA | AGATGCATCT | TATACCAAGG | CCCTTAAGTT | ATTTGAAGAT | 1500 |
| AAAGAACTTC | AGTGGACCTT | CATAATGCTG | ACCTACCTGA | ATAACACACT | GGTAGAAGAT | 1560 |
| TGTGTCAAAG | TTCGATCAGC | AGCTGTTACC | TGTTTGAAAA | ACATTTTAGC | CACAAAGACT | 1620 |
| GGACATAGTT | TCTGGGAGAT | TTATAAGATG | ACAACAGATC | CAATGCTGGC | CTATCTACAG | 1680 |
| CCTTTTAGAA | CATCAAGAAA | AAAGTTTTTA | GAAGTACCCA | GATTTGACAA | AGAAAACCCT | 1740 |
| TTTGAAGGCC | TGGATGATAT | AAATCTGTGG | ATTCCTCTAA | GTGAAAATCA | TGACATTTGG | 1800 |
| ATAAAGACAC | TGACTTGTGC | TTTTTTGGAC | AGTGGAGGCA | CAAAATGTGA | AATTCTTCAA | 1860 |
| TTATTAAAGC | CAATGTGTGA | AGTGAAAACT | GACTTTGTC | AGACTGTACT | TCCATACTTG | 1920 |
| ATTCATGATA | TTTTACTCCA | AGATACAAAT | GAATCATGGA | GAAATCTGCT | TTCTACACAT | 1980 |
| GTTCAGGGAT | TTTTCACCAG | CTGTCTTCGA | CACTTCTCGC | AAACGAGCCG | ATCCACAACC | 2040 |

-continued

```
CCTGCAAACT TGGATTCAGA GTCAGAGCAC TTTTTCCGAT GCTGTTTGGA TAAAAAATCA  2100
CAAAGAACAA TGCTTGCTGT TGTGGACTAC ATGAGAAGAC AAAAGAGACC TTCTTCAGGA  2160
ACAATTTTTA ATGATGCTTT CTGGCTGGAT TTAAATTATC TAGAAGTTGC CAAGGTAGCT  2220
CAGTCTTGTG CTGCTCACTT TACAGCTTTA CTCTATGCAG AAATCTATGC AGATAAGAAA  2280
AGTATGGATG ATCAAGAGAA AAGAAGTCTT GCATTTGAAG AAGGAAGCCA GAGTACAACT  2340
ATTTCTAGCT TGAGTGAAAA AAGTAAAGAA GAAACTGGAA TAAGTTTACA GGATCTTCTC  2400
TTAGAAATCT ACAGAAGTAT AGGGGAGCCA GATAGTTTGT ATGGCTGTGG TGGAGGGAAG  2460
ATGTTACAAC CCATTACTAG ACTACGAACA TATGAACACG AAGCAATGTG GGCAAAGCC   2520
CTAGTAACAT ATGACCTCGA AACAGCAATC CCCTCATCAA CACGCCAGGC AGGAATCATT  2580
CAGGCCTTGC AGAATTTGGG ACTCTGCCAT ATTCTTTCCG TCTATTTAAA AGGATTGGAT  2640
TATGAAAATA AAGACTGGTG TCCTGAACTA GAAGAACTTC ATTACCAAGC AGCATGGAGG  2700
AATATGCAGT GGGACCATTG CACTTCCGTC AGCAAAGAAG TAGAAGGAAC CAGTTACCAT  2760
GAATCATTGT ACAATGCTCT ACAATCTCTA AGAGACAGAG AATTCTCTAC ATTTTATGAA  2820
AGTCTCAAAT ATGCCAGAGT AAAAGAAGTG GAAGAGATGT GTAAGCGCAG CCTTGAGTCT  2880
GTGTATTCGC TCTATCCCAC ACTTAGCAGG TTGCAGGCCA TTGGAGAGCT GGAAAGCATT  2940
GGGGAGCTTT TCTCAAGATC AGTCACACAT AGACAACTCT CTGAAGTATA TATTAAGTGG  3000
CAGAAACACT CCCAGCTTCT CAAGGACAGT GATTTTAGTT TTCAGGAGCC TATCATGGCT  3060
CTACGCACAG TCATTTTGGA GATCCTGATG GAAAAGGAAA TGGACAACTC ACAAAGAGAA  3120
TGTATTAAGG ACATTCTCAC CAAACACCTT GTAGAACTCT CTATACTGGC CAGAACTTTC  3180
AAGAACACTC AGCTCCCTGA AGGGCAATA TTTCAAATTA AACAGTACAA TTCAGTTAGC   3240
TGTGGAGTCT CTGAGTGGCA GCTGGAAGAA GCACAAGTAT TCTGGGCAAA AAAGGAGCAG  3300
AGTCTTGCCC TGAGTATTCT CAAGCAAATG ATCAAGAAGT TGGATGCCAG CTGTGCAGCG  3360
AACAATCCCA GCCTAAAACT TACATACACA GAATGTCTGA GGGTTTGTGG CAACTGGTTA  3420
GCAGAAACGT GCTTAGAAAA TCCTGCGGTC ATCATGCAGA CCTATCTAGA AAAGGCAGTA  3480
GAAGTTGCTG GAAATTATGA TGGAGAAAGT AGTGATGAGC TAAGAAATGG AAAAATGAAG  3540
GCATTTCTCT CATTAGCCCG GTTTTCAGAT ACTCAATACC AAAGAATTGA AAACTACATG  3600
AAATCATCGG AATTTGAAAA CAAGCAAGCT CTCCTGAAAA GAGCCAAAGA GGAAGTAGGT  3660
CTCCTTAGGG AACATAAAAT TCAGACAAAC AGATACACAG TAAAGGTTCA GCGAGAGCTG  3720
GAGTTGGATG AATTAGCCCT GCGTGCACTG AAAGAGGATC GTAAACGCTT CTTATGTAAA  3780
GCAGTTGAAA ATTATATCAA CTGCTTATTA AGTGGAGAAG AACATGATAT GTGGGTATTC  3840
CGACTTTGTT CCCTCTGGCT TGAAAATTCT GGAGTTTCTG AAGTCAATGG CATGATGAAG  3900
AGAGACGGAA TGAAGATTCC AACATATAAA TTTTTGCCTC TTATGTACCA ATTGGCTGCT  3960
AGAATGGGGA CCAAGATGAT GGGAGGCCTA GGATTTCATG AAGTCCTCAA TAATCTAATC  4020
TCTAGAATTT CAATGGATCA CCCCCATCAC ACTTTGTTTA TTATACTGGC CTTAGCAAAT  4080
GCAAACAGAG ATGAATTTCT GACTAAACCA GAGGTAGCCA GAAGAAGCAG ATAACTAAA   4140
AATGTGCCTA ACAAAGCTC TCAGCTTGAT GAGGATCGAA CAGAGGCTGC AAATAGAATA   4200
ATATGTACTA TCAGAAGTAG GAGACCTCAG ATGGTCAGAA GTGTTGAGGC ACTTTGTGAT  4260
GCTTATATTA TATTAGCAAA CTTAGATGCC ACTCAGTGGA AGACTCAGAG AAAAGGCATA  4320
AATATTCCAG CAGACCAGCC AATTACTAAA CTTAAGAATT TAGAAGATGT TGTTGTCCCT  4380
ACTATGGAAA TTAAGGTGGA CCACACAGGA GAATATGGAA ATCTGGTGAC TATACAGTCA  4440
```

-continued

| | | | | | |
|---|---|---|---|---|---|
| TTTAAAGCAG | AATTTCGCTT | AGCAGGAGGT | GTAAATTTAC | CAAAAATAAT | AGATTGTGTA | 4500
| GGTTCCGATG | GCAAGGAGAG | GAGACAGCTT | GTTAAGGGCC | GTGATGACCT | GAGACAAGAT | 4560
| GCTGTCATGC | AACAGGTCTT | CCAGATGTGT | AATACATTAC | TGCAGAGAAA | CACGGAAACT | 4620
| AGGAAGAGGA | AATTAACTAT | CTGTACTTAT | AAGGTGGTTC | CCCTCTCTCA | GCGAAGTGGT | 4680
| GTTCTTGAAT | GGTGCACAGG | AACTGTCCCC | ATTGGTGAAT | TTCTTGTTAA | CAATGAAGAT | 4740
| GGTGCTCATA | AAAGATACAG | GCCAAATGAT | TTCAGTGCCT | TTCAGTGCCA | AAAGAAAATG | 4800
| ATGGAGGTGC | AAAAAAAGTC | TTTTGAAGAG | AAATATGAAG | TCTTCATGGA | TGTTTGCCAA | 4860
| AATTTTCAAC | CAGTTTTCCG | TTACTTCTGC | ATGGAAAAAT | TCTTGGATCC | AGCTATTTGG | 4920
| TTTGAGAAGC | GATTGGCTTA | TACGCGCAGT | GTAGCTACTT | CTTCTATTGT | TGGTTACATA | 4980
| CTTGGACTTG | GTGATAGACA | TGTACAGAAT | ATCTTGATAA | ATGAGCAGTC | AGCAGAACTT | 5040
| GTACATATAG | ATCTAGGTGT | TGCTTTTGAA | CAGGGCAAAA | TCCTTCCTAC | TCCTGAGACA | 5100
| GTTCCTTTTA | GACTCACCAG | AGATATTGTG | GATGGCATGG | GCATTACGGG | TGTTGAAGGT | 5160
| GTCTTCAGAA | GATGCTGTGA | GAAAACCATG | GAAGTGATGA | GAAACTCTCA | GGAAACTCTG | 5220
| TTAACCATTG | TAGAGGTAAA | GTATTTTATA | AGGAAGACTT | TATTTTTTTT | CTTACCAGGT | 5280
| AGACTGTGTA | TCTCATCAGG | AAGTCACTGA | TGTGAAGAGC | ACTGCTTCAT | TTTAACATAG | 5340
| GGGGATGTGG | CTGGGCAGCA | GAAAGGAGGA | GATTGTGCAC | TTAGCCTTTT | CACACATCCA | 5400
| AAAATACTGG | TTTAGAAATG | CCTTCAGCCC | CCTTGAGTTT | CTTGGAATGT | TAGAGCATTG | 5460
| TAAGTAGTCT | CTAGTTTTCA | ATTCATAAAT | CAATTCTTTG | ACATTTAGAT | ATTCCATATG | 5520
| GTATTATTAT | TTTTAGAATG | GTTTCCATTA | GGGTTTACGA | AAAATCAGAA | ATTTATATCT | 5580
| CCTCTTTCCC | TGCTCAGGTT | CAGAACTAAT | TAGTCAGACA | AAATGGAGAT | CAAAATTGGT | 5640
| CAGCATCATT | ACTAGAGGGA | CATGGCTTAG | GAATTGAGGG | CCAAGACTAG | TTTACCTGCT | 5700
| GGTGCTACCC | TCAAGTACCC | TCCTGCTGT | CTTAACTTTG | GGACAAGCTC | ACCCTGAATA | 5760
| GGGGTTGGGC | CTGCAGAGCA | AACACATGTA | ATCAGGATCA | CTGCCTTGTC | TTGATCCAGG | 5820
| GCAGAAAAAA | GGAAGTCAAA | CAAATTTCAG | TGTCTGTGCT | GTTAGTACCT | ATGCCAGTCA | 5880
| TTCACCAATC | TGGTAAGGGT | ATGTGAGACA | AGAAATCAGG | AGTGTGGCCT | CCCCAGGGAA | 5940
| GCATGGCAGG | TAGAGTGCAG | TATGGGCTTG | CCACTTTTCC | ACTACTCAGC | TTTTCTTCCT | 6000
| TTAACCTGAT | TTATGTTGGA | CTGGCTGCAT | GTTAGTATTA | CTTTTACTGC | ATTTAAAAAA | 6060
| CATTGATGCT | GATCAAATTC | AAACCAGGTT | TCTAGAGATG | GGGCAGGAAT | ATGTGCATTT | 6120
| TTAAAAATCT | CTCCTACTGT | TCCACTAGGA | TATGAGAACT | GTCTTAATTC | ATTGGCATTA | 6180
| ACCATTAAGC | CTGTGGTCAA | TAAGGGTGGG | CCTTTATCCC | TTGGAAGATG | AGTAACAGTC | 6240
| CATCAGGGTG | GTCCTGTGTG | CACCTTTATG | AACCGAGGCA | TCTTTATAGA | TCTCCTTTGG | 6300
| ACTGCAGGTG | GTAATACAGA | TTTTGCTACA | AGGAGTTTGC | TGAAATAGGT | CCCAATAATA | 6360
| CGTTGGTAAA | ATTAAATCCA | AGNCTGTGCT | ATTCCCAAGG | TTAAAAATAC | ATTCTTTTTT | 6420
| CTTTTACCGA | TTTCAAATTC | TGTTCATACA | TGTTGTCATT | TGTTACAGTT | TGCCATTGGT | 6480
| TCTGCAGTAA | GAATAAATGA | TAAGAAAATA | AAAAAAAAAA | AAAAA | | 6525

( 2 ) INFORMATION FOR SEQ ID NO:4:

( i ) SEQUENCE CHARACTERISTICS:
      ( A ) LENGTH: 15 amino acids
      ( B ) TYPE: amino acid
      ( C ) STRANDEDNESS: single
      ( D ) TOPOLOGY: linear ( x i ) SEQUENCE DESCRIPTION: SEQ ID NO:4:

His Glu Pro Ala Asn Ser Ser Ala Ser Gln Ser Thr Asp Leu Cys
1               5                   10                  15

(2) INFORMATION FOR SEQ ID NO:5:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:5:

Cys Lys Arg Asn Leu Ser Asp Ile Asp Gln Ser Phe Asp Lys Val
1               5                   10                  15

(2) INFORMATION FOR SEQ ID NO:6:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO:6:

Pro Glu Asp Glu Thr Glu Leu His Pro Thr Leu Asn Ala Asp Asp Gln
1               5                   10                  15

Glu Cys (2) INFORMATION FOR SEQ ID NO:7:

(i) SEQUENCE CHARACTERISTICS:
        (A) LENGTH: 26 amino acids
        (B) TYPE: amino acid
        (C) STRANDEDNESS: single
        (D) TOPOLOGY: linear (xi) SEQUENCE DESCRIPTION: SEQ ID NO:7:

Cys Lys Ser Leu Ala Ser Phe Ile Lys Lys Pro Phe Asp Arg Gly Glu
1               5                   10                  15

Val Glu Ser Met Glu Asp Asp Thr Asn Gly
                20                  25

(2) INFORMATION FOR SEQ ID NO:8:

(i) SEQUENCE CHARACTERISTICS:
        (A) LENGTH: 3056 amino acids
        (B) TYPE: amino acid
        (C) STRANDEDNESS: single
        (D) TOPOLOGY: linear (xi) SEQUENCE DESCRIPTION: SEQ ID NO:8:

Met Ser Leu Val Leu Asn Asp Leu Leu Ile Cys Cys Arg Gln Leu Glu
1               5                   10                  15

His Asp Arg Ala Thr Glu Arg Lys Lys Glu Val Glu Lys Phe Lys Arg
                20                  25                  30

Leu Ile Arg Asp Pro Glu Thr Ile Lys His Leu Asp Arg His Ser Asp
                35                  40                  45

Ser Lys Gln Gly Lys Tyr Leu Asn Trp Asp Ala Val Phe Arg Phe Leu
        50                  55                  60

Gln Lys Tyr Ile Gln Lys Glu Thr Glu Cys Leu Arg Ile Ala Lys Pro
65                  70                  75                  80

Asn Val Ser Ala Ser Thr Gln Ala Ser Arg Gln Lys Lys Met Gln Glu
                85                  90                  95

```
Ile  Ser  Ser  Leu  Val  Lys  Tyr  Phe  Ile  Lys  Cys  Ala  Asn  Arg  Ala
          100                 105                      110

Pro  Arg  Leu  Lys  Cys  Gln  Glu  Leu  Leu  Asn  Tyr  Ile  Met  Asp  Thr  Val
          115                 120                      125

Lys  Asp  Ser  Ser  Asn  Gly  Ala  Ile  Tyr  Gly  Ala  Asp  Cys  Ser  Asn  Ile
          130                 135                      140

Leu  Leu  Lys  Asp  Ile  Leu  Ser  Val  Arg  Lys  Tyr  Trp  Cys  Glu  Ile  Ser
145                      150                 155                           160

Gln  Gln  Gln  Trp  Leu  Glu  Leu  Phe  Ser  Val  Tyr  Phe  Arg  Leu  Tyr  Leu
                    165                 170                      175

Lys  Pro  Ser  Gln  Asp  Val  His  Arg  Val  Leu  Val  Ala  Arg  Ile  Ile  His
               180                      185                      190

Ala  Val  Thr  Lys  Gly  Cys  Cys  Ser  Gln  Thr  Asp  Gly  Leu  Asn  Ser  Lys
               195                 200                      205

Phe  Leu  Asp  Phe  Phe  Ser  Lys  Ala  Ile  Gln  Cys  Ala  Arg  Gln  Glu  Lys
          210                 215                      220

Ser  Ser  Ser  Gly  Leu  Asn  His  Ile  Leu  Ala  Ala  Leu  Thr  Ile  Phe  Leu
225                      230                 235                           240

Lys  Thr  Leu  Ala  Val  Asn  Phe  Arg  Ile  Arg  Val  Cys  Glu  Leu  Gly  Asp
                    245                 250                           255

Glu  Ile  Leu  Pro  Thr  Leu  Val  Tyr  Ile  Trp  Thr  Gln  His  Arg  Leu  Asn
               260                 265                      270

Asp  Ser  Leu  Lys  Glu  Val  Ile  Glu  Leu  Phe  Gln  Leu  Gln  Ile  Tyr
          275                 280                 285

Ile  His  His  Pro  Lys  Gly  Ala  Lys  Thr  Gln  Glu  Lys  Gly  Ala  Tyr  Glu
     290                 295                      300

Ser  Thr  Lys  Trp  Arg  Ser  Ile  Leu  Tyr  Asn  Leu  Tyr  Asp  Leu  Leu  Val
305                      310                 315                           320

Asn  Glu  Ile  Ser  His  Ile  Gly  Ser  Arg  Gly  Lys  Tyr  Ser  Ser  Gly  Phe
                    325                 330                           335

Arg  Asn  Ile  Ala  Val  Lys  Glu  Asn  Leu  Ile  Glu  Leu  Met  Ala  Asp  Ile
               340                 345                      350

Cys  His  Gln  Val  Phe  Asn  Glu  Asp  Thr  Arg  Ser  Leu  Glu  Ile  Ser  Gln
          355                 360                      365

Ser  Tyr  Thr  Thr  Thr  Gln  Arg  Glu  Ser  Ser  Asp  Tyr  Ser  Val  Pro  Cys
     370                 375                      380

Lys  Arg  Lys  Lys  Ile  Glu  Leu  Gly  Trp  Glu  Val  Ile  Lys  Asp  His  Leu
385                      390                 395                           400

Gln  Lys  Ser  Gln  Asn  Asp  Phe  Asp  Leu  Val  Pro  Trp  Leu  Gln  Ile  Ala
               405                 410                      415

Thr  Gln  Leu  Ile  Ser  Lys  Tyr  Pro  Ala  Ser  Leu  Pro  Asn  Cys  Glu  Leu
               420                 425                      430

Ser  Pro  Leu  Leu  Met  Ile  Leu  Ser  Gln  Leu  Leu  Pro  Gln  Gln  Arg  His
          435                 440                      445

Gly  Glu  Arg  Thr  Pro  Tyr  Val  Leu  Arg  Cys  Leu  Thr  Glu  Val  Ala  Leu
     450                 455                      460

Cys  Gln  Asp  Lys  Arg  Ser  Asn  Leu  Glu  Ser  Ser  Gln  Lys  Ser  Asp  Leu
465                 470                      475                           480

Leu  Lys  Leu  Trp  Asn  Lys  Ile  Trp  Cys  Ile  Thr  Phe  Arg  Gly  Ile  Ser
                    485                 490                           495

Ser  Glu  Gln  Lys  Gln  Ala  Glu  Asn  Phe  Gly  Leu  Leu  Gly  Ala  Ile  Ile
               500                 505                      510

Gln  Gly  Ser  Leu  Val  Glu  Val  Asp  Arg  Glu  Phe  Trp  Lys  Leu  Phe  Thr
          515                 520                      525
```

```
Gly Ser Ala Cys Arg Pro Ser Cys Pro Ala Val Cys Cys Leu Thr Leu
    530                 535                 540
Ala Leu Thr Thr Ser Ile Val Pro Gly Ala Val Lys Met Gly Ile Glu
545                 550                 555                 560
Gln Asn Met Cys Glu Val Asn Arg Ser Phe Ser Leu Lys Glu Ser Ile
                565                 570                 575
Met Lys Trp Leu Leu Phe Tyr Gln Leu Glu Gly Asp Leu Glu Asn Ser
            580                 585                 590
Thr Glu Val Pro Pro Ile Leu His Ser Asn Phe Pro His Leu Val Leu
        595                 600                 605
Glu Lys Ile Leu Val Ser Leu Thr Met Lys Asn Cys Lys Ala Ala Met
    610                 615                 620
Asn Phe Phe Gln Ser Val Pro Glu Cys Glu His His Lys Asp Lys
625                 630                 635                 640
Glu Glu Leu Ser Phe Ser Glu Val Glu Glu Leu Phe Leu Gln Thr Thr
                645                 650                 655
Phe Asp Lys Met Asp Phe Leu Thr Ile Val Arg Glu Cys Gly Ile Glu
            660                 665                 670
Lys His Gln Ser Ser Ile Gly Phe Ser Val His Gln Asn Leu Lys Glu
        675                 680                 685
Ser Leu Asp Arg Cys Leu Leu Gly Leu Ser Glu Gln Leu Leu Asn Asn
    690                 695                 700
Tyr Ser Ser Glu Ile Thr Asn Ser Glu Thr Leu Val Arg Cys Ser Arg
705                 710                 715                 720
Leu Leu Val Gly Val Leu Gly Cys Tyr Cys Tyr Met Gly Val Ile Ala
                725                 730                 735
Glu Glu Glu Ala Tyr Lys Ser Glu Leu Phe Gln Lys Ala Asn Ser Leu
            740                 745                 750
Met Gln Cys Ala Gly Glu Ser Ile Thr Leu Phe Lys Asn Lys Thr Asn
        755                 760                 765
Glu Glu Phe Arg Ile Gly Ser Leu Arg Asn Met Met Gln Leu Cys Thr
    770                 775                 780
Arg Cys Leu Ser Asn Cys Thr Lys Lys Ser Pro Asn Lys Ile Ala Ser
785                 790                 795                 800
Gly Phe Phe Leu Arg Leu Leu Thr Ser Lys Leu Met Asn Asp Ile Ala
                805                 810                 815
Asp Ile Cys Lys Ser Leu Ala Ser Phe Ile Lys Lys Pro Phe Asp Arg
            820                 825                 830
Gly Glu Val Glu Ser Met Glu Asp Thr Asn Gly Asn Leu Met Glu
        835                 840                 845
Val Glu Asp Gln Ser Ser Met Asn Leu Phe Asn Asp Tyr Pro Asp Ser
    850                 855                 860
Ser Val Ser Asp Ala Asn Glu Pro Gly Glu Ser Gln Ser Thr Ile Gly
865                 870                 875                 880
Ala Ile Asn Pro Leu Ala Glu Glu Tyr Leu Ser Lys Gln Asp Leu Leu
                885                 890                 895
Phe Leu Asp Met Leu Lys Phe Leu Cys Leu Cys Val Thr Thr Ala Gln
            900                 905                 910
Thr Asn Thr Val Ser Phe Arg Ala Ala Asp Ile Arg Arg Lys Leu Leu
        915                 920                 925
Met Leu Ile Asp Ser Ser Thr Leu Glu Pro Thr Lys Ser Leu His Leu
    930                 935                 940
His Met Tyr Leu Met Leu Leu Lys Glu Leu Pro Gly Glu Glu Tyr Pro
```

-continued

| | 945 | | | | | 950 | | | | | 955 | | | | 960 |
|---|---|---|---|---|---|---|---|---|---|---|---|---|---|---|---|
| Leu | Pro | Met | Glu | Asp | Val | Leu | Glu | Leu | Leu | Lys | Pro | Leu | Ser | Asn | Val |
| | | | | 965 | | | | | 970 | | | | | 975 | |
| Cys | Ser | Leu | Tyr | Arg | Arg | Asp | Gln | Asp | Val | Cys | Lys | Thr | Ile | Leu | Asn |
| | | | | 980 | | | | | 985 | | | | | 990 | |
| His | Val | Leu | His | Val | Val | Lys | Asn | Leu | Gly | Gln | Ser | Asn | Met | Asp | Ser |
| | | | | 995 | | | | | 1000 | | | | | 1005 | |
| Glu | Asn | Thr | Arg | Asp | Ala | Gln | Gly | Gln | Phe | Leu | Thr | Val | Ile | Gly | Ala |
| | | | 1010 | | | | | 1015 | | | | | 1020 | | |
| Phe | Trp | His | Leu | Thr | Lys | Glu | Arg | Lys | Tyr | Ile | Phe | Ser | Val | Arg | Met |
| 1025 | | | | | 1030 | | | | | 1035 | | | | | 1040 |
| Ala | Leu | Val | Asn | Cys | Leu | Lys | Thr | Leu | Leu | Glu | Ala | Asp | Pro | Tyr | Ser |
| | | | | 1045 | | | | | 1050 | | | | | 1055 | |
| Lys | Trp | Ala | Ile | Leu | Asn | Val | Met | Gly | Lys | Asp | Phe | Pro | Val | Asn | Glu |
| | | | | 1060 | | | | | 1065 | | | | | 1070 | |
| Val | Phe | Thr | Gln | Phe | Leu | Ala | Asp | Asn | His | His | Gln | Val | Arg | Met | Leu |
| | | | | 1075 | | | | | 1080 | | | | | 1085 | |
| Ala | Ala | Glu | Ser | Ile | Asn | Arg | Leu | Phe | Gln | Asp | Thr | Lys | Gly | Asp | Ser |
| | | | | 1090 | | | | | 1095 | | | | | 1100 | |
| Ser | Arg | Leu | Leu | Lys | Ala | Leu | Pro | Leu | Lys | Leu | Gln | Gln | Thr | Ala | Phe |
| 1105 | | | | | 1110 | | | | | 1115 | | | | | 1120 |
| Glu | Asn | Ala | Tyr | Leu | Lys | Ala | Gln | Glu | Gly | Met | Arg | Glu | Met | Ser | His |
| | | | | 1125 | | | | | 1130 | | | | | 1135 | |
| Ser | Ala | Glu | Asn | Pro | Glu | Thr | Leu | Asp | Glu | Ile | Tyr | Asn | Arg | Lys | Ser |
| | | | | 1140 | | | | | 1145 | | | | | 1150 | |
| Val | Leu | Leu | Thr | Leu | Ile | Ala | Val | Val | Leu | Ser | Cys | Ser | Pro | Ile | Cys |
| | | | | 1155 | | | | | 1160 | | | | | 1165 | |
| Glu | Lys | Gln | Ala | Leu | Phe | Ala | Leu | Cys | Lys | Ser | Val | Lys | Glu | Asn | Gly |
| | | | | 1170 | | | | | 1175 | | | | | 1180 | |
| Leu | Glu | Pro | His | Leu | Val | Lys | Lys | Val | Leu | Glu | Lys | Val | Ser | Glu | Thr |
| 1185 | | | | | 1190 | | | | | 1195 | | | | | 1200 |
| Phe | Gly | Tyr | Arg | Arg | Leu | Glu | Asp | Phe | Met | Ala | Ser | His | Leu | Asp | Tyr |
| | | | | 1205 | | | | | 1210 | | | | | 1215 | |
| Leu | Val | Leu | Glu | Trp | Leu | Asn | Leu | Gln | Asp | Thr | Glu | Tyr | Asn | Leu | Ser |
| | | | | 1220 | | | | | 1225 | | | | | 1230 | |
| Ser | Phe | Pro | Phe | Ile | Leu | Leu | Asn | Tyr | Thr | Asn | Ile | Glu | Asp | Phe | Tyr |
| | | | | 1235 | | | | | 1240 | | | | | 1245 | |
| Arg | Ser | Cys | Tyr | Lys | Val | Leu | Ile | Pro | His | Leu | Val | Ile | Arg | Ser | His |
| | | | 1250 | | | | | 1255 | | | | | 1260 | | |
| Phe | Asp | Glu | Val | Lys | Ser | Ile | Ala | Asn | Gln | Ile | Gln | Glu | Asp | Trp | Lys |
| 1265 | | | | | 1270 | | | | | 1275 | | | | | 1280 |
| Ser | Leu | Leu | Thr | Asp | Cys | Phe | Pro | Lys | Ile | Leu | Val | Asn | Ile | Leu | Pro |
| | | | | 1285 | | | | | 1290 | | | | | 1295 | |
| Tyr | Phe | Ala | Tyr | Glu | Gly | Thr | Arg | Asp | Ser | Gly | Met | Ala | Gln | Gln | Arg |
| | | | | 1300 | | | | | 1305 | | | | | 1310 | |
| Glu | Thr | Ala | Thr | Lys | Val | Tyr | Asp | Met | Leu | Lys | Ser | Glu | Asn | Leu | Leu |
| | | | | 1315 | | | | | 1320 | | | | | 1325 | |
| Gly | Lys | Gln | Ile | Asp | His | Leu | Phe | Ile | Ser | Asn | Leu | Pro | Glu | Ile | Val |
| | | | | 1330 | | | | | 1335 | | | | | 1340 | |
| Val | Glu | Leu | Leu | Met | Thr | Leu | His | Glu | Pro | Ala | Asn | Ser | Ser | Ala | Ser |
| 1345 | | | | | 1350 | | | | | 1355 | | | | | 1360 |
| Gln | Ser | Thr | Asp | Leu | Cys | Asp | Phe | Ser | Gly | Asp | Leu | Asp | Pro | Ala | Pro |
| | | | | 1365 | | | | | 1370 | | | | | 1375 | |

```
Asn  Pro  Pro  His  Phe  Pro  Ser  His  Val  Ile  Lys  Ala  Thr  Phe  Ala  Tyr
               1380            1385                      1390

Ile  Ser  Asn  Cys  His  Lys  Thr  Lys  Leu  Lys  Ser  Ile  Leu  Glu  Ile  Leu
          1395                 1400                      1405

Ser  Lys  Ser  Pro  Asp  Ser  Tyr  Gln  Lys  Ile  Leu  Leu  Ala  Ile  Cys  Glu
     1410                     1415                 1420

Gln  Ala  Ala  Glu  Thr  Asn  Asn  Val  Tyr  Lys  Lys  His  Arg  Ile  Leu  Lys
1425                1430                1435                          1440

Ile  Tyr  His  Leu  Phe  Val  Ser  Leu  Leu  Leu  Lys  Asp  Ile  Lys  Ser  Gly
               1445                     1450                          1455

Leu  Gly  Gly  Ala  Trp  Ala  Phe  Val  Leu  Arg  Asp  Val  Ile  Tyr  Thr  Leu
               1460                1465                      1470

Ile  His  Tyr  Ile  Asn  Gln  Arg  Pro  Ser  Cys  Ile  Met  Asp  Val  Ser  Leu
               1475                1480                      1485

Arg  Ser  Phe  Ser  Leu  Cys  Cys  Asp  Leu  Leu  Ser  Gln  Val  Cys  Gln  Thr
     1490                1495                      1500

Ala  Val  Thr  Tyr  Cys  Lys  Asp  Ala  Leu  Glu  Asn  His  Leu  His  Val  Ile
1505                1510                1515                          1520

Val  Gly  Thr  Leu  Ile  Pro  Leu  Val  Tyr  Glu  Gln  Val  Glu  Val  Gln  Lys
               1525                1530                      1535

Gln  Val  Leu  Asp  Leu  Leu  Lys  Tyr  Leu  Val  Ile  Asp  Asn  Lys  Asp  Asn
          1540                1545                      1550

Glu  Asn  Leu  Tyr  Ile  Thr  Ile  Lys  Leu  Leu  Asp  Pro  Phe  Pro  Asp  His
          1555                1560                      1565

Val  Val  Phe  Lys  Asp  Leu  Arg  Ile  Thr  Gln  Gln  Lys  Ile  Lys  Tyr  Ser
1570                     1575                     1580

Arg  Gly  Pro  Phe  Ser  Leu  Leu  Glu  Glu  Ile  Asn  His  Phe  Leu  Ser  Val
1585                1590                1595                          1600

Ser  Val  Tyr  Asp  Ala  Leu  Pro  Leu  Thr  Arg  Leu  Glu  Gly  Leu  Lys  Asp
               1605                1610                      1615

Leu  Arg  Arg  Gln  Leu  Glu  Leu  His  Lys  Asp  Gln  Met  Val  Asp  Ile  Met
               1620                1625                      1630

Arg  Ala  Ser  Gln  Asp  Asn  Pro  Gln  Asp  Gly  Ile  Met  Val  Lys  Leu  Val
     1635                1640                      1645

Val  Asn  Leu  Leu  Gln  Leu  Ser  Lys  Met  Ala  Ile  Asn  His  Thr  Gly  Glu
          1650                1655                      1660

Lys  Glu  Val  Leu  Glu  Ala  Val  Gly  Ser  Cys  Leu  Gly  Glu  Val  Gly  Pro
1665                1670                1675                          1680

Ile  Asp  Phe  Ser  Thr  Ile  Ala  Ile  Gln  His  Ser  Lys  Asp  Ala  Ser  Tyr
               1685                1690                      1695

Thr  Lys  Ala  Leu  Lys  Leu  Phe  Glu  Asp  Lys  Glu  Leu  Gln  Trp  Thr  Phe
               1700                1705                      1710

Ile  Met  Leu  Thr  Tyr  Leu  Asn  Asn  Thr  Leu  Val  Glu  Asp  Cys  Val  Lys
               1715                1720                      1725

Val  Arg  Ser  Ala  Ala  Val  Thr  Cys  Leu  Lys  Asn  Ile  Leu  Ala  Thr  Lys
          1730                1735                      1740

Thr  Gly  His  Ser  Phe  Trp  Glu  Ile  Tyr  Lys  Met  Thr  Thr  Asp  Pro  Met
1745                1750                1755                          1760

Leu  Ala  Tyr  Leu  Gln  Pro  Phe  Arg  Thr  Ser  Arg  Lys  Lys  Phe  Leu  Glu
               1765                1770                      1775

Val  Pro  Arg  Phe  Asp  Lys  Glu  Asn  Pro  Phe  Glu  Gly  Leu  Asp  Asp  Ile
               1780                1785                      1790

Asn  Leu  Trp  Ile  Pro  Leu  Ser  Glu  Asn  His  Asp  Ile  Trp  Ile  Lys  Thr
               1795                1800                      1805
```

-continued

```
Leu Thr Cys Ala Phe Leu Asp Ser Gly Gly Thr Lys Cys Glu Ile Leu
    1810                1815                1820
Gln Leu Leu Lys Pro Met Cys Glu Val Lys Thr Asp Phe Cys Gln Thr
1825                1830                1835                1840
Val Leu Pro Tyr Leu Ile His Asp Ile Leu Gln Asp Thr Asn Glu
            1845                1850                1855
Ser Trp Arg Asn Leu Leu Ser Thr His Val Gln Gly Phe Phe Thr Ser
            1860                1865                1870
Cys Leu Arg His Phe Ser Gln Thr Ser Arg Ser Thr Thr Pro Ala Asn
        1875                1880                1885
Leu Asp Ser Glu Ser Glu His Phe Phe Arg Cys Cys Leu Asp Lys Lys
        1890                1895                1900
Ser Gln Arg Thr Met Leu Ala Val Val Asp Tyr Met Arg Arg Gln Lys
1905                1910                1915                1920
Arg Pro Ser Ser Gly Thr Ile Phe Asn Asp Ala Phe Trp Leu Asp Leu
            1925                1930                1935
Asn Tyr Leu Glu Val Ala Lys Val Ala Gln Ser Cys Ala Ala His Phe
            1940                1945                1950
Thr Ala Leu Leu Tyr Ala Glu Ile Tyr Ala Asp Lys Lys Ser Met Asp
        1955                1960                1965
Asp Gln Glu Lys Arg Ser Leu Ala Phe Glu Glu Gly Ser Gln Ser Thr
1970                1975                1980
Thr Ile Ser Ser Leu Ser Glu Lys Ser Lys Glu Glu Thr Gly Ile Ser
1985                1990                1995                2000
Leu Gln Asp Leu Leu Leu Glu Ile Tyr Arg Ser Ile Gly Glu Pro Asp
            2005                2010                2015
Ser Leu Tyr Gly Cys Gly Gly Gly Lys Met Leu Gln Pro Ile Thr Arg
            2020                2025                2030
Leu Arg Thr Tyr Glu His Glu Ala Met Trp Gly Lys Ala Leu Val Thr
        2035                2040                2045
Tyr Asp Leu Glu Thr Ala Ile Pro Ser Ser Thr Arg Gln Ala Gly Ile
        2050                2055                2060
Ile Gln Ala Leu Gln Asn Leu Gly Leu Cys His Ile Leu Ser Val Tyr
2065                2070                2075                2080
Leu Lys Gly Leu Asp Tyr Glu Asn Lys Asp Trp Cys Pro Glu Leu Glu
            2085                2090                2095
Glu Leu His Tyr Gln Ala Ala Trp Arg Asn Met Gln Trp Asp His Cys
        2100                2105                2110
Thr Ser Val Ser Lys Glu Val Glu Gly Thr Ser Tyr His Glu Ser Leu
        2115                2120                2125
Tyr Asn Ala Leu Gln Ser Leu Arg Asp Arg Glu Phe Ser Thr Phe Tyr
    2130                2135                2140
Glu Ser Leu Lys Tyr Ala Arg Val Lys Glu Val Glu Glu Met Cys Lys
2145                2150                2155                2160
Arg Ser Leu Glu Ser Val Tyr Ser Leu Tyr Pro Thr Leu Ser Arg Leu
            2165                2170                2175
Gln Ala Ile Gly Glu Leu Glu Ser Ile Gly Glu Leu Phe Ser Arg Ser
        2180                2185                2190
Val Thr His Arg Gln Leu Ser Glu Val Tyr Ile Lys Trp Gln Lys His
        2195                2200                2205
Ser Gln Leu Leu Lys Asp Ser Asp Phe Ser Phe Gln Glu Pro Ile Met
    2210                2215                2220
Ala Leu Arg Thr Val Ile Leu Glu Ile Leu Met Glu Lys Glu Met Asp
```

```
     2225                 2230                  2235                    2240
Asn  Ser  Gln  Arg  Glu  Cys  Ile  Lys  Asp  Ile  Leu  Thr  Lys  His  Leu  Val
                    2245                      2250                  2255
Glu  Leu  Ser  Ile  Leu  Ala  Arg  Thr  Phe  Lys  Asn  Thr  Gln  Leu  Pro  Glu
                    2260                      2265                  2270
Arg  Ala  Ile  Phe  Gln  Ile  Lys  Gln  Tyr  Asn  Ser  Val  Ser  Cys  Gly  Val
                    2275                      2280                  2285
Ser  Glu  Trp  Gln  Leu  Glu  Glu  Ala  Gln  Val  Phe  Trp  Ala  Lys  Lys  Glu
                    2290                      2295                  2300
Gln  Ser  Leu  Ala  Leu  Ser  Ile  Leu  Lys  Gln  Met  Ile  Lys  Lys  Leu  Asp
2305                      2310                      2315                 2320
Ala  Ser  Cys  Ala  Ala  Asn  Asn  Pro  Ser  Leu  Lys  Leu  Thr  Tyr  Thr  Glu
                    2325                      2330                  2335
Cys  Leu  Arg  Val  Cys  Gly  Asn  Trp  Leu  Ala  Glu  Thr  Cys  Leu  Glu  Asn
                    2340                      2345                  2350
Pro  Ala  Val  Ile  Met  Gln  Thr  Tyr  Leu  Glu  Lys  Ala  Val  Glu  Val  Ala
                    2355                      2360                  2365
Gly  Asn  Tyr  Asp  Gly  Glu  Ser  Ser  Asp  Glu  Leu  Arg  Asn  Gly  Lys  Met
                    2370                      2375                  2380
Lys  Ala  Phe  Leu  Ser  Leu  Ala  Arg  Phe  Ser  Asp  Thr  Gln  Tyr  Gln  Arg
2385                      2390                      2395                 2400
Ile  Glu  Asn  Tyr  Met  Lys  Ser  Ser  Glu  Phe  Glu  Asn  Lys  Gln  Ala  Leu
                    2405                      2410                  2415
Leu  Lys  Arg  Ala  Lys  Glu  Glu  Val  Gly  Leu  Leu  Arg  Glu  His  Lys  Ile
                    2420                      2425                  2430
Gln  Thr  Asn  Arg  Tyr  Thr  Val  Lys  Val  Gln  Arg  Glu  Leu  Glu  Leu  Asp
                    2435                      2440                  2445
Glu  Leu  Ala  Leu  Arg  Ala  Leu  Lys  Glu  Asp  Arg  Lys  Arg  Phe  Leu  Cys
                    2450                      2455                  2460
Lys  Ala  Val  Glu  Asn  Tyr  Ile  Asn  Cys  Leu  Leu  Ser  Gly  Glu  Glu  His
2465                      2470                      2475                 2480
Asp  Met  Trp  Val  Phe  Arg  Leu  Cys  Ser  Leu  Trp  Leu  Glu  Asn  Ser  Gly
                    2485                      2490                  2495
Val  Ser  Glu  Val  Asn  Gly  Met  Met  Lys  Arg  Asp  Gly  Met  Lys  Ile  Pro
                    2500                      2505                  2510
Thr  Tyr  Lys  Phe  Leu  Pro  Leu  Met  Tyr  Gln  Leu  Ala  Ala  Arg  Met  Gly
                    2515                      2520                  2525
Thr  Lys  Met  Met  Gly  Gly  Leu  Gly  Phe  His  Glu  Val  Leu  Asn  Asn  Leu
                    2530                      2535                  2540
Ile  Ser  Arg  Ile  Ser  Met  Asp  His  Pro  His  His  Thr  Leu  Phe  Ile  Ile
2545                      2550                      2555                 2560
Leu  Ala  Leu  Ala  Asn  Ala  Asn  Arg  Asp  Glu  Phe  Leu  Thr  Lys  Pro  Glu
                    2565                      2570                  2575
Val  Ala  Arg  Arg  Ser  Arg  Ile  Thr  Lys  Asn  Val  Pro  Lys  Gln  Ser  Ser
                    2580                      2585                  2590
Gln  Leu  Asp  Glu  Asp  Arg  Thr  Glu  Ala  Ala  Asn  Arg  Ile  Ile  Cys  Thr
                    2595                      2600                  2605
Ile  Arg  Ser  Arg  Arg  Pro  Gln  Met  Val  Arg  Ser  Val  Glu  Ala  Leu  Cys
                    2610                      2615                  2620
Asp  Ala  Tyr  Ile  Ile  Leu  Ala  Asn  Leu  Asp  Ala  Thr  Gln  Trp  Lys  Thr
2625                      2630                      2635                 2640
Gln  Arg  Lys  Gly  Ile  Asn  Ile  Pro  Ala  Asp  Gln  Pro  Ile  Thr  Lys  Leu
                    2645                      2650                  2655
```

```
Lys Asn Leu Glu Asp Val Val Val Pro Thr Met Glu Ile Lys Val Asp
                2660                2665                2670
His Thr Gly Glu Tyr Gly Asn Leu Val Thr Ile Gln Ser Phe Lys Ala
            2675                2680                2685
Glu Phe Arg Leu Ala Gly Gly Val Asn Leu Pro Lys Ile Ile Asp Cys
        2690                2695                2700
Val Gly Ser Asp Gly Lys Glu Arg Arg Gln Leu Val Lys Gly Arg Asp
2705                2710                2715                2720
Asp Leu Arg Gln Asp Ala Val Met Gln Gln Val Phe Gln Met Cys Asn
                2725                2730                2735
Thr Leu Leu Gln Arg Asn Thr Glu Thr Arg Lys Arg Lys Leu Thr Ile
                2740                2745                2750
Cys Thr Tyr Lys Val Val Pro Leu Ser Gln Arg Ser Gly Val Leu Glu
            2755                2760                2765
Trp Cys Thr Gly Thr Val Pro Ile Gly Glu Phe Leu Val Asn Asn Glu
        2770                2775                2780
Asp Gly Ala His Lys Arg Tyr Arg Pro Asn Asp Phe Ser Ala Phe Gln
2785                2790                2795                2800
Cys Gln Lys Lys Met Met Glu Val Gln Lys Lys Ser Phe Glu Glu Lys
                2805                2810                2815
Tyr Glu Val Phe Met Asp Val Cys Gln Asn Phe Gln Pro Val Phe Arg
            2820                2825                2830
Tyr Phe Cys Met Glu Lys Phe Leu Asp Pro Ala Ile Trp Phe Glu Lys
        2835                2840                2845
Arg Leu Ala Tyr Thr Arg Ser Val Ala Thr Ser Ser Ile Val Gly Tyr
    2850                2855                2860
Ile Leu Gly Leu Gly Asp Arg His Val Gln Asn Ile Leu Ile Asn Glu
2865                2870                2875                2880
Gln Ser Ala Glu Leu Val His Ile Asp Leu Gly Val Ala Phe Glu Gln
                2885                2890                2895
Gly Lys Ile Leu Pro Thr Pro Glu Thr Val Pro Phe Arg Leu Thr Arg
            2900                2905                2910
Asp Ile Val Asp Gly Met Gly Ile Thr Gly Val Glu Gly Val Phe Arg
        2915                2920                2925
Arg Cys Cys Glu Lys Thr Met Glu Val Met Arg Asn Ser Gln Glu Thr
    2930                2935                2940
Leu Leu Thr Ile Val Glu Val Leu Leu Tyr Asp Pro Leu Phe Asp Trp
2945                2950                2955                2960
Thr Met Asn Pro Leu Lys Ala Leu Tyr Leu Gln Gln Arg Pro Glu Asp
                2965                2970                2975
Glu Thr Glu Leu His Pro Thr Leu Asn Ala Asp Asp Gln Glu Cys Lys
            2980                2985                2990
Arg Asn Leu Ser Asp Ile Asp Gln Ser Phe Asp Lys Val Ala Glu Arg
        2995                3000                3005
Val Leu Met Arg Leu Gln Glu Lys Leu Lys Gly Val Glu Glu Gly Thr
    3010                3015                3020
Val Leu Ser Val Gly Gly Gln Val Asn Leu Leu Ile Gln Gln Ala Ile
3025                3030                3035                3040
Asp Pro Lys Asn Leu Ser Arg Leu Phe Pro Gly Trp Lys Ala Trp Val
                3045                3050                3055
```

( 2 ) INFORMATION FOR SEQ ID NO:9:

( i ) SEQUENCE CHARACTERISTICS:

( A ) LENGTH: 9870 base pairs ( B ) TYPE: nucleic acid
( C ) STRANDEDNESS: single
( D ) TOPOLOGY: linear ( x i ) SEQUENCE DESCRIPTION: SEQ ID NO:9:

```
ATCTGCGCTG CCTTCCGAGT GCAGTGAGGC CCTTCCGAGT GCAGTGAGGC ATACATCACA    60
ATTTGGAATT ATGCATTGGT TTATCAATTT ACTTGTTTAT TGTCACCCTG CTGCCCAGAT   120
ATGACTTCAT GAGGACAGTG ATGTGTGTTC TGAAATTGTG AACCATGAGT CTAGTACTTA   180
ATGATCTGCT TATCTGCTGC CGTCAACTAG AACATGATAG AGCTACAGAA CGAAAGAAAG   240
AAGTTGAGAA ATTTAAGCGC CTGATTCGAG ATCCTGAAAC AATTAAACAT CTAGATCGGC   300
ATTCAGATTC CAAACAAGGA AAATATTTGA ATTGGGATGC TGTTTTTAGA TTTTTACAGA   360
AATATATTCA GAAAGAAACA GAATGTCTGA GAATAGCAAA ACCAAATGTA TCAGCCTCAA   420
CACAAGCCTC CAGGCAGAAA AAGATGCAGG AAATCAGTAG TTTGGTCAAA TACTTCATCA   480
AATGTGCAAA CAGAAGAGCA CCTAGGCTAA AATGTCAAGA ACTCTTAAAT TATATCATGG   540
ATACAGTGAA AGATTCATCT AATGGTGCTA TTTACGGAGC TGATTGTAGC AACATACTAC   600
TCAAAGACAT TCTTTCTGTG AGAAAATACT GGTGTGAAAT ATCTCAGCAA CAGTGGTTAG   660
AATTGTTCTC TGTGTACTTC AGGCTCTATC TGAAACCTTC ACAAGATGTT CATAGAGTTT   720
TAGTGGCTAG AATAATTCAT GCTGTTACCA AAGGATGCTG TTCTCAGACT GACGGATTAA   780
ATTCCAAATT TTTGGACTTT TTTTCCAAGG CTATTCAGTG TGCGAGACAA GAAAAGAGCT   840
CTTCAGGTCT AAATCATATC TTAGCAGCTC TTACTATCTT CCTCAAGACT TTGGCTGTCA   900
ACTTTCGAAT TCGAGTGTGT GAATTAGGAG ATGAAATTCT TCCCACTTTG GTTTATATTT   960
GGACTCAACA TAGGCTTAAT GATTCTTTAA AGAAGTCAT TATTGAATTA TTTCAACTGC   1020
AAATTTATAT CCATCATCCG AAAGGAGCCA AAACCCAAGA AAAAGGTGCT TATGAATCAA   1080
CAAAATGGAG AAGTATTTTA TACAACTTAT ATGATCTGCT AGTGAATGAG ATAAGTCATA   1140
TAGGAAGTAG AGGAAAGTAT TCTTCAGGAT TTCGTAATAT TGCCGTCAAA GAAAATTTGA   1200
TTGAATTGAT GGCAGATATC TGTCACCAGG TTTTTAATGA AGATACCAGA TCCTTGGAGA   1260
TTTCTCAATC TTACACTACT ACACAAAGAG AATCTAGTGA TTACAGTGTC CCTTGCAAAA   1320
GGAAGAAAAT AGAACTAGGC TGGGAAGTAA TAAAAGATCA CCTTCAGAAG TCACAGAATG   1380
ATTTTGATCT TGTGCCTTGG CTACAGATTG CAACCCAATT AATATCAAAG TATCCTGCAA   1440
GTTACCTAA CTGTGAGCTG TCTCCATTAC TGATGATACT ATCTCAGCTT CTACCCCAAC   1500
AGCGACATGG GGAACGTACA CCATATGTGT TACGATGCCT TACGGAAGTT GCATTGTGTC   1560
AAGACAAGAG GTCAAACCTA GAAAGCTCAC AAAAGTCAGA TTTATTAAAA CTCTGGAATA   1620
AAATTTGGTG TATTACCTTT CGTGGTATAA GTTCTGAGCA AAAACAAGCT GAAAACTTTG   1680
GCTTACTTGG AGCCATAATT CAGGGTAGTT TAGTTGAGGT TGACAGAGAA TTCTGGAAGT   1740
TATTTACTGG GTCAGCCTGC AGACCTTCAT GTCCTGCAGT ATGCTGTTTG ACTTGGCAC   1800
TGACCACCAG TATAGTTCCA GGAGCGGTAA AAATGGGAAT AGAGCAAAAT ATGTGTGAAG   1860
TAAATAGAAG CTTTCTTTA AAGGAATCAA TAATGAAATG GCTCTTATTC TATCAGTTAG   1920
AGGGTGACTT AGAAAATAGC ACAGAAGTGC CTCCAATTCT TCACAGTAAT TTTCCTCATC   1980
TTGTACTGGA GAAAATTCTT GTGAGTCTCA CTATGAAAAA CTGTAAAGCT GCAATGAATT   2040
TTTTCCAAAG CGTGCCAGAA TGTAACACC ACCACAAAGA TAAAGAAGAA CTTTCATTCT   2100
CAGAAGTAGA AGAACTATTT CTTCAGACAA CTTTTGACAA GATGGACTTT TTAACCATTG   2160
TGAGAGAATG TGGTATAGAA AAGCACCAGT CCAGTATTGG CTTCTCTGTC CACCAGAATC   2220
```

| | | | | | |
|---|---|---|---|---|---|
| TCAAGGAATC | ACTGGATCGC | TGTCTTCTGG | GATTATCAGA | ACAGCTTCTG | AATAATTACT | 2280
| CATCTGAGAT | TACAAATTCA | GAAACTCTTG | TCCGGTGTTC | ACGTCTTTTG | GTGGGTGTCC | 2340
| TTGGCTGCTA | CTGTTACATG | GGTGTAATAG | CTGAAGAGGA | AGCATATAAG | TCAGAATTAT | 2400
| TCCAGAAAGC | CAACTCTCTA | ATGCAATGTG | CAGGAGAAAG | TATCACTCTG | TTTAAAAATA | 2460
| AGACAAATGA | GGAATTCAGA | ATTGGTTCCT | TGAGAAATAT | GATGCAGCTA | TGTACACGTT | 2520
| GCTTGAGCAA | CTGTACCAAG | AAGAGTCCAA | ATAAGATTGC | ATCTGGCTTT | TTCCTGCGAT | 2580
| TGTTAACATC | AAAGCTAATG | AATGACATTG | CAGATATTTG | TAAAAGTTTA | GCATCCTTCA | 2640
| TCAAAAAGCC | ATTTGACCGT | GGAGAAGTAG | AATCAATGGA | AGATGATACT | AATGGAAATC | 2700
| TAATGGAGGT | GGAGGATCAG | TCATCCATGA | ATCTATTTAA | CGATTACCCT | GATAGTAGTG | 2760
| TTAGTGATGC | AAACGAACCT | GGAGAGAGCC | AAAGTACCAT | AGGTGCCATT | AATCCTTTAG | 2820
| CTGAAGAATA | TCTGTCAAAG | CAAGATCTAC | TTTTCTTAGA | CATGCTCAAG | TTCTTGTGTT | 2880
| TGTGTGTAAC | TACTGCTCAG | ACCAATACTG | TGTCCTTTAG | GGCAGCTGAT | ATTCGGAGGA | 2940
| AATTGTTAAT | GTTAATTGAT | TCTAGCACGC | TAGAACCTAC | CAAATCCCTC | CACCTGCATA | 3000
| TGTATCTAAT | GCTTTTAAAG | GAGCTTCCTG | GAGAAGAGTA | CCCCTTGCCA | ATGGAAGATG | 3060
| TTCTTGAACT | TCTGAAACCA | CTATCCAATG | TGTGTTCTTT | GTATCGTCGT | GACCAAGATG | 3120
| TTTGTAAAAC | TATTTTAAAC | CATGTCCTTC | ATGTAGTGAA | AAACCTAGGT | CAAAGCAATA | 3180
| TGGACTCTGA | GAACACAAGG | GATGCTCAAG | GACAGTTTCT | TACAGTAATT | GGAGCATTTT | 3240
| GGCATCTAAC | AAAGGAGAGG | AAATATATAT | TCTCTGTAAG | AATGGCCCTA | GTAAATTGCC | 3300
| TTAAAACTTT | GCTTGAGGCT | GATCCTTATT | CAAAATGGGC | CATTCTTAAT | GTAATGGGAA | 3360
| AAGACTTTCC | TGTAAATGAA | GTATTTACAC | AATTTCTTGC | TGACAATCAT | CACCAAGTTC | 3420
| GCATGTTGGC | TGCAGAGTCA | ATCAATAGAT | TGTTCCAGGA | CACGAAGGGA | GATTCTTCCA | 3480
| GGTTACTGAA | AGCACTTCCT | TTGAAGCTTC | AGCAAACAGC | TTTTGAAAAT | GCATACTTGA | 3540
| AAGCTCAGGA | AGGAATGAGA | GAAATGTCCC | ATAGTGCTGA | GAACCCTGAA | ACTTTGGATG | 3600
| AAATTTATAA | TAGAAAATCT | GTTTTACTGA | CGTTGATAGC | TGTGGTTTTA | TCCTGTAGCC | 3660
| CTATCTGCGA | AAAACAGGCT | TTGTTTGCCC | TGTGTAAATC | TGTGAAAGAG | AATGGATTAG | 3720
| AACCTCACCT | TGTGAAAAAG | GTTTTAGAGA | AAGTTCTGA | AACTTTTGGA | TATAGACGTT | 3780
| TAGAAGACTT | TATGGCATCT | CATTTAGATT | ATCTGGTTTT | GGAATGGCTA | AATCTTCAAG | 3840
| ATACTGAATA | CAACTTATCT | TCTTTTCCTT | TTATTTTATT | AAACTACACA | AATATTGAGG | 3900
| ATTTCTATAG | ATCTTGTTAT | AAGGTTTTGA | TTCCACATCT | GGTGATTAGA | AGTCATTTTG | 3960
| ATGAGGTGAA | GTCCATTGCT | AATCAGATTC | AAGAGGACTG | GAAAAGTCTT | CTAACAGACT | 4020
| GCTTTCCAAA | GATTCTTGTA | AATATTCTTC | CTTATTTTGC | CTATGAGGGT | ACCAGAGACA | 4080
| GTGGGATGGC | ACAGCAAAGA | GAGACTGCTA | CCAAGGTCTA | TGATATGCTT | AAAAGTGAAA | 4140
| ACTTATTGGG | AAAACAGATT | GATCACTTAT | TCATTAGTAA | TTTACCAGAG | ATTGTGGTGG | 4200
| AGTTATTGAT | GACGTTACAT | GAGCCAGCAA | ATTCTAGTGC | CAGTCAGAGC | ACTGACCTCT | 4260
| GTGACTTTTC | AGGGGATTTG | GATCCTGCTC | CTAATCCACC | TCATTTTCCA | TCGCATGTGA | 4320
| TTAAAGCAAC | ATTTGCCTAT | ATCAGCAATT | GTCATAAAAC | CAAGTTAAAA | AGCATTTTAG | 4380
| AAATTCTTTC | CAAAAGCCCT | GATTCCTATC | AGAAAATTCT | TCTTGCCATA | TGTGAGCAAG | 4440
| CAGCTGAAAC | AAATAATGTT | TATAAGAAGC | ACAGAATTCT | TAAAATATAT | CACCTGTTTG | 4500
| TTAGTTTATT | ACTGAAAGAT | ATAAAAAGTG | GCTTAGGAGG | AGCTTGGGCC | TTTGTTCTTC | 4560
| GAGACGTTAT | TTATACTTTG | ATTCACTATA | TCAACCAAAG | GCCTTCTTGT | ATCATGGATG | 4620

| | | | | | |
|---|---|---|---|---|---|
| TGTCATTACG | TAGCTTCTCC | CTTGTTGTG | ACTTATTAAG | TCAGGTTTGC | CAGACAGCCG | 4680 |
| TGACTTACTG | TAAGGATGCT | CTAGAAAACC | ATCTTCATGT | TATTGTTGGT | ACACTTATAC | 4740 |
| CCCTTGTGTA | TGAGCAGGTG | GAGGTTCAGA | AACAGGTATT | GGACTTGTTG | AAATACTTAG | 4800 |
| TGATAGATAA | CAAGGATAAT | GAAAACCTCT | ATATCACGAT | TAAGCTTTTA | GATCCTTTTC | 4860 |
| CTGACCATGT | TGTTTTTAAG | GATTGCGTA | TTACTCAGCA | AAAAATCAAA | TACAGTAGAG | 4920 |
| GACCCTTTTC | ACTCTTGGAG | GAAATTAACC | ATTTTCTCTC | AGTAAGTGTT | TATGATGCAC | 4980 |
| TTCCATTGAC | AAGACTTGAA | GGACTAAAGG | ATCTTCGAAG | ACAACTGGAA | CTACATAAAG | 5040 |
| ATCAGATGGT | GGACATTATG | AGAGCTTCTC | AGGATAATCC | GCAAGATGGG | ATTATGGTGA | 5100 |
| AACTAGTTGT | CAATTTGTTG | CAGTTATCCA | AGATGGCAAT | AAACCACACT | GGTGAAAAAG | 5160 |
| AAGTTCTAGA | GGCTGTTGGA | AGCTGCTTGG | GAGAAGTGGG | TCCTATAGAT | TTCTCTACCA | 5220 |
| TAGCTATACA | ACATAGTAAA | GATGCATCTT | ATACCAAGGC | CCTTAAGTTA | TTTGAAGATA | 5280 |
| AAGAACTTCA | GTGGACCTTC | ATAATGCTGA | CCTACCTGAA | TAACACACTG | GTAGAAGATT | 5340 |
| GTGTCAAAGT | TCGATCAGCA | GCTGTTACCT | GTTGAAAAA | CATTTAGCC | ACAAAGACTG | 5400 |
| GACATAGTTT | CTGGGAGATT | TATAAGATGA | CAACAGATCC | AATGCTGGCC | TATCTACAGC | 5460 |
| CTTTTAGAAC | ATCAAGAAAA | AAGTTTTTAG | AAGTACCCAG | ATTTGACAAA | GAAAACCCTT | 5520 |
| TTGAAGGCCT | GGATGATATA | AATCTGTGGA | TTCCTCTAAG | TGAAAATCAT | GACATTTGGA | 5580 |
| TAAAGACACT | GACTTGTGCT | TTTTTGGACA | GTGGAGGCAC | AAAATGTGAA | ATTCTTCAAT | 5640 |
| TATTAAAGCC | AATGTGTGAA | GTGAAAACTG | ACTTTTGTCA | GACTGTACTT | CCATACTTGA | 5700 |
| TTCATGATAT | TTTACTCCAA | GATACAAATG | AATCATGGAG | AAATCTGCTT | TCTACACATG | 5760 |
| TTCAGGGATT | TTTCACCAGC | TGTCTTCGAC | ACTTCTCGCA | AACGAGCCGA | TCCACAACCC | 5820 |
| CTGCAAACTT | GGATTCAGAG | TCAGAGCACT | TTTTCCGATG | CTGTTTGGAT | AAAAAATCAC | 5880 |
| AAAGAACAAT | GCTTGCTGTT | GTGGACTACA | TGAGAAGACA | AAAGAGACCT | TCTTCAGGAA | 5940 |
| CAATTTTTAA | TGATGCTTTC | TGGCTGGATT | TAAATTATCT | AGAAGTTGCC | AAGGTAGCTC | 6000 |
| AGTCTTGTGC | TGCTCACTTT | ACAGCTTTAC | TCTATGCAGA | AATCTATGCA | GATAAGAAAA | 6060 |
| GTATGGATGA | TCAAGAGAAA | AGAAGTCTTG | CATTTGAAGA | AGGAAGCCAG | AGTACAACTA | 6120 |
| TTTCTAGCTT | GAGTGAAAAA | AGTAAAGAAG | AAACTGGAAT | AAGTTTACAG | GATCTTCTCT | 6180 |
| TAGAAATCTA | CAGAAGTATA | GGGGAGCCAG | ATAGTTTGTA | TGGCTGTGGT | GGAGGGAAGA | 6240 |
| TGTTACAACC | CATTACTAGA | CTACGAACAT | ATGAACACGA | AGCAATGTGG | GGCAAAGCCC | 6300 |
| TAGTAACATA | TGACCTCGAA | ACAGCAATCC | CCTCATCAAC | ACGCCAGGCA | GGAATCATTC | 6360 |
| AGGCCTTGCA | GAATTTGGGA | CTCTGCCATA | TTCTTTCCGT | CTATTTAAAA | GGATTGGATT | 6420 |
| ATGAAAATAA | AGACTGGTGT | CCTGAACTAG | AAGAACTTCA | TTACCAAGCA | GCATGGAGGA | 6480 |
| ATATGCAGTG | GGACCATTGC | ACTTCCGTCA | GCAAAGAAGT | AGAAGGAACC | AGTTACCATG | 6540 |
| AATCATTGTA | CAATGCTCTA | CAATCTCTAA | GAGACAGAGA | ATTCTCTACA | TTTTATGAAA | 6600 |
| GTCTCAAATA | TGCCAGAGTA | AAAGAAGTGG | AAGAGATGTG | TAAGCGCAGC | CTTGAGTCTG | 6660 |
| TGTATTCGCT | CTATCCCACA | CTTAGCAGGT | TGCAGGCCAT | GGAGAGCTG | GAAAGCATTG | 6720 |
| GGGAGCTTTT | CTCAAGATCA | GTCACACATA | GACAACTCTC | TGAAGTATAT | ATTAAGTGGC | 6780 |
| AGAAACACTC | CCAGCTTCTC | AAGGACAGTG | ATTTTAGTTT | TCAGGAGCCT | ATCATGGCTC | 6840 |
| TACGCACAGT | CATTTTGGAG | ATCCTGATGG | AAAAGGAAAT | GGACAACTCA | CAAAGAGAAT | 6900 |
| GTATTAAGGA | CATTCTCACC | AAACACCTTG | TAGAACTCTC | TATACTGGCC | AGAACTTTCA | 6960 |
| AGAACACTCA | GCTCCCTGAA | AGGGCAATAT | TTCAAATTAA | ACAGTACAAT | TCAGTTAGCT | 7020 |

```
GTGGAGTCTC TGAGTGGCAG CTGGAAGAAG CACAAGTATT CTGGGCAAAA AAGGAGCAGA    7080
GTCTTGCCCT GAGTATTCTC AAGCAAATGA TCAAGAAGTT GGATGCCAGC TGTGCAGCGA    7140
ACAATCCCAG CCTAAAACTT ACATACACAG AATGTCTGAG GGTTTGTGGC AACTGGTTAG    7200
CAGAAACGTG CTTAGAAAAT CCTGCGGTCA TCATGCAGAC CTATCTAGAA AAGGCAGTAG    7260
AAGTTGCTGG AAATTATGAT GGAGAAAGTA GTGATGAGCT AAGAAATGGA AAAATGAAGG    7320
CATTTCTCTC ATTAGCCCGG TTTTCAGATA CTCAATACCA AAGAATTGAA AACTACATGA    7380
AATCATCGGA ATTTGAAAAC AAGCAAGCTC TCCTGAAAAG AGCCAAAGAG GAAGTAGGTC    7440
TCCTTAGGGA ACATAAAATT CAGACAAACA GATACACAGT AAAGGTTCAG CGAGAGCTGG    7500
AGTTGGATGA ATTAGCCCTG CGTGCACTGA AAGAGGATCG TAAACGCTTC TTATGTAAAG    7560
CAGTTGAAAA TTATATCAAC TGCTTATTAA GTGGAGAAGA ACATGATATG TGGGTATTCC    7620
GGCTTTGTTC CCTCTGGCTT GAAAATTCTG GAGTTTCTGA AGTCAATGGC ATGATGAAGA    7680
GAGACGGAAT GAAGATTCCA ACATATAAAT TTTTGCCTCT TATGTACCAA TTGGCTGCTA    7740
GAATGGGGAC CAAGATGATG GGAGGCCTAG GATTTCATGA AGTCCTCAAT AATCTAATCT    7800
CTAGAATTTC AATGGATCAC CCCCATCACA CTTTGTTTAT TATACTGGCC TTAGCAAATG    7860
CAAACAGAGA TGAATTTCTG ACTAAACCAG AGGTAGCCAG AAGAAGCAGA ATAACTAAAA    7920
ATGTGCCTAA ACAAAGCTCT CAGCTTGATG AGGATCGAAC AGAGGCTGCA AATAGAATAA    7980
TATGTACTAT CAGAAGTAGG AGACCTCAGA TGGTCAGAAG TGTTGAGGCA CTTTGTGATG    8040
CTTATATTAT ATTAGCAAAC TTAGATGCCA CTCAGTGGAA GACTCAGAGA AAAGGCATAA    8100
ATATTCCAGC AGACCAGCCA ATTACTAAAC TTAAGAATTT AGAAGATGTT GTTGTCCCTA    8160
CTATGGAAAT TAAGGTGGAC CACACAGGAG AATATGGAAA TCTGGTGACT ATACAGTCAT    8220
TTAAAGCAGA ATTTCGCTTA GCAGGAGGTG TAAATTTACC AAAAATAATA GATTGTGTAG    8280
GTTCCGATGG CAAGGAGAGG AGACAGCTTG TTAAGGGCCG TGATGACCTG AGACAAGATG    8340
CTGTCATGCA ACAGGTCTTC CAGATGTGTA ATACATTACT GCAGAGAAAC ACGGAAACTA    8400
GGAAGAGGAA ATTAACTATC TGTACTTATA AGGTGGTTCC CCTCTCTCAG CGAAGTGGTG    8460
TTCTTGAATG GTGCACAGGA ACTGTCCCCA TTGGTGAATT TCTTGTTAAC AATGAAGATG    8520
GTGCTCATAA AGATACAGG CCAAATGATT TCAGTGCCTT TCAGTGCCAA AAGAAAATGA    8580
TGGAGGTGCA AAAAAAGTCT TTTGAAGAGA AATATGAAGT CTTCATGGAT GTTTGCCAAA    8640
ATTTTCAACC AGTTTTCCGT TACTTCTGCA TGGAAAAATT CTTGGATCCA GCTATTTGGT    8700
TTGAGAAGCG ATTGGCTTAT ACGCGCAGTG TAGCTACTTC TTCTATTGTT GGTTACATAC    8760
TTGGACTTGG TGATAGACAT GTACAGAATA TCTTGATAAA TGAGCAGTCA GCAGAACTTG    8820
TACATATAGA TCTAGGTGTT GCTTTTGAAC AGGGCAAAAT CCTTCCTACT CCTGAGACAG    8880
TTCCTTTTAG ACTCACCAGA GATATTGTGG ATGGCATGGG CATTACGGGT GTTGAAGGTG    8940
TCTTCAGAAG ATGCTGTGAG AAAACCATGG AAGTGATGAG AAACTCTCAG GAAACTCTGT    9000
TAACCATTGT AGAGGTCCTT CTATATGATC CACTCTTTGA CTGGACCATG AATCCTTTGA    9060
AAGCTTTGTA TTTACAGCAG AGGCCGGAAG ATGAAACTGA GCTTCACCCT ACTCTGAATG    9120
CAGATGACCA AGAATGCAAA CGAAATCTCA GTGATATTGA CCAGAGTTTC GACAAAGTAG    9180
CTGAACGTGT CTTAATGAGA CTACAAGAGA AACTGAAAGG AGTGGAAGAA GGCACTGTGC    9240
TCAGTGTTGG TGGACAGGTG AATTTGCTCA TACAGCAGGC CATAGACCCC AAAAATCTCA    9300
GCCGACTTTT CCCAGGATGG AAAGCTTGGG TGTGATCTTC AGTATATGAA TTACCCTTTC    9360
ATTCAGCCTT TAGAAATTAT ATTTTAGCCT TTATTTTTAA CCTGCCAACA TACTTTAAGT    9420
```

| | | | | | | |
|---|---|---|---|---|---|---|
|AGGGATTAAT|ATTTAAGTGA|ACTATTGTGG|GTTTTTTTGA|ATGTTGGTTT|TAATACTTGA|9480|
|TTTAATCACC|ACTCAAAAAT|GTTTTGATGG|TCTTAAGGAA|CATCTCTGCT|TTCACTCTTT|9540|
|AGAAATAATG|GTCATTCGGG|CTGGGCGCAG|CGGCTCACGC|CTGTAATCCC|AGCACTTTGG|9600|
|GAGGCCGAGG|TGAGCGGATC|ACAAGGTCAG|GAGTTCGAGA|CCAGCCTGGC|CAAGAGACCA|9660|
|GCCTGGCCAG|TATGGTGAAA|CCCTGTCTCT|ACTAAAAATA|CAAAAATTAG|CCGAGCATGG|9720|
|TGGCGGGCAC|CTGTAGTCCC|AGCTACTCGA|GAGGCTGAGG|CAGGAGAATC|TCTTGAACCT|9780|
|GGGAGGTGAA|GGTTGCTGTG|GGCCAAAATC|ATGCCATTGC|ACTCCAGCCT|GGGTGACAAG|9840|
|AGCGAAACTC|CATCTCAAAA|AAAAAAAAAA| | | |9870|

CDNAS ASSOCIATED WITH ATAXIA-TELANGIECTASIA

This application is a Continuation-In-Part of U.S. Ser. No. 08/493,092, filed Jun. 21, 1995, which is a Continuation-In-Part of U.S. Ser. No. 08/441,822, filed May 16, 1995.

GRANT SUPPORT

This work was supported in part by grants from the National Institutes of Health, United States-Israel Binational Science Foundation, A-T Medical Research Foundation, A-T Medical Trust, and the A-T Children's Project.

TECHNICAL FIELD

The present invention relates to the determination of the gene sequence, mutations of which cause ataxia-telangiectasia (A-T), designated ATM, and the use of the gene and gene products in detection of carriers of the A-T gene, and preparing native and transgenic organisms in which the gene products encoded by the ATM gene or its homolog in other species are artificially produced, or the expression of the native ATM gene is modified.

BACKGROUND OF THE INVENTION

Ataxia-telangiectasia (A-T) is a progressive genetic disorder affecting the central nervous and immune systems, and involving chromosomal instability, cancer predisposition, radiation sensitivity, and cell cycle abnormalities. Studies of the cellular phenotype of A-T have pointed to a defect in a putative system that processes a specific type of DNA damage and initiates a signal transduction pathway controlling replication and repair. For a general review of Ataxia-telangiectasia, reference is hereby made to the review *Ataxia-Telangiectasis: Closer to Unraveling the Mystery*, Eur. J. Hum. Genet. (Shiloh, 1995) which, along with its cited references, is hereby incorporated by reference.

Despite extensive investigation over the last two decades, A-T has remained a clinical and molecular enigma. A-T is a multi-system disease inherited in an autosomal recessive manner, with a worldwide frequency of 1:100,000 live births and an estimated carrier frequency of 1% in the American population. Notable concentrations of A-T patients outside the United States are in Turkey, Italy and Israel. Israeli A-T patients are Moroccan Jews, Palestinian Arabs, Bedouins and Druzes.

Cerebellar ataxia that gradually develops into general motor dysfunction is the first clinical hallmark and results from progressive loss of Purkinje cells in the cerebellum. Oculocutaneous telangiectasia (dilation of blood vessels) develops in the bulbar conjunctiva and facial skin, and is later accompanied by graying of the hair and atrophic changes in the skin. Somatic growth is retarded in most patients, and ovarian dysgenesis is typical for female patients. Among occasional endocrine abnormalities, insulin-resistant diabetes is predominant, and serum levels of alpha-fetoprotein and carcinoembryonic antigen are elevated. The thymus is either absent or vestigial, and other immunological defects include reduced levels of serum IgA, IgE or IgG2, peripheral lymphopenia, and reduced responses to viral antigens and allogeneic cells, that cause many patients to suffer from recurrent sinopulmonary infections.

Cancer predisposition in A-T is striking: 38% of patients develop malignancies, mainly lymphoreticular neoplasms and leukemias. But, A-T patients manifest acute radiosensitivity and must be treated with reduced radiation doses, and not with radiomimetic chemotherapy. The most common cause of death in A-T, typically during the second or third decade of life, is sinopulmonary infections with or without malignancy.

The complexity of the disease is reflected also in the cellular phenotype. Chromosomal instability is expressed as increased chromosomal breakage and the appearance in lymphocytes of clonal translocations specifically involving the loci of the immune system genes. Such clones may later become predominant when a lymphoreticular malignancy appears. Primary fibroblast lines from A-T patients show accelerated senescence, increased demand for certain growth factors, and defective cytoskeletal structure. Most notable is the abnormal response of A-T cells to ionizing radiation and certain radiomimetic chemicals. While hypersensitive to the cytotoxic and clastogenic effects of these agents, DNA synthesis is inhibited by these agents to a lesser extent than in normal cells. The concomitant lack of radiation-induced cell cycle delay and reduction of radiation-induced elevation of p53 protein are evidence of a defect in a cell cycle checkpoint. Increased intrachromosomal recombination in A-T cells was also noted recently.

Prenatal diagnoses of A-T using cytogenetic analysis or measurements of DNA synthesis have been reported, but these tests are laborious and subject to background fluctuations and, therefore, not widely used.

A-T homozygotes have two defective copies of the A-T gene and are affected with the disease. A-T heterozygotes (carriers) have one normal copy of the gene and one defective copy of the gene and are generally healthy. When two carriers have children, there is a 25% risk in every pregnancy of giving birth to an A-T affected child.

A-T heterozygotes show a significant excess of various malignancies, with a 3- to 4-fold increased risk for all cancers between the ages of 20 and 80, and a 5-fold increased risk of breast cancer in women. These observations turn A-T into a public health problem and add an important dimension to A-T research, particularly to heterozygote identification. Cultured cells from A-T heterozygotes indeed show an intermediate degree of X-ray sensitivity, but the difference from normal cells is not always large enough to warrant using this criterion as a laboratory assay for carrier detection. The main reason for the unreliability of this assay is the various degrees of overlap between A-T heterozygotes and non-heterozygotes with respect to radiosensitivity. Cytogenetic assays for carriers have the same problems as for prenatal diagnosis, they are labor intensive and not always consistent.

The nature of the protein missing in A-T is unknown. Cell fusion studies have established four complementation groups in A-T, designated A, C, D and E, suggesting the probable involvement of at least four genes or four types of mutations in one gene, with inter-allelic complementation. These four groups are clinically indistinguishable and were found to account for 55%, 28%, 14% and 3% of some 80 patients typed to date. In Israel, several Moroccan Jewish patients were assigned to group C, while Palestinian Arab patients were assigned to group A.

The general chromosomal localization of the putative A-T gene(s) has been determined, but not the sequence. An A-T locus containing the A-T(A) mutations was localized by Gatti et al. (1988) to chromosome 11, region q22-23, using linkage analysis. The A-T(C) locus was localized by applicant to the same region of chromosome 11, region q22-23, by linkage analysis of an extended Jewish Moroccan A-T family (Ziv et al., 1991). Further studies, conducted by an international consortium in which applicant participated (McConville et al., 1990; Foroud et al., 1991; Ziv et al., 1992), reconfirmed this localization in a series of studies and gradually narrowed the A-T locus to an interval estimated at 4 centimorgan, which probably contains also the A-T(E) mutations.

A proposed gene for complementation group D is disclosed in U.S. Pat. No. 5,395,767 to Murnane et al., issued Mar. 7, 1995. This sequence was found not to be mutated in any complementation group of A-T. Further, the gene sequence was mapped physically distant from the presumptive A-T locus.

Therefore, in order to better understand the nature and effects of A-T, as well as to more accurately and consistently determine those individuals who may carry the defective gene for A-T, it would be advantageous to isolate and determine the gene sequence, mutations of which are responsible for causing A-T, and utilize this sequence as a basis for detecting carriers of A-T and thereby be able to more beneficially manage the underlying conditions and predispositions of those carriers of the defective gene.

SUMMARY OF THE INVENTION AND ADVANTAGES

According to the present invention, a gene sequence and mutations of this sequence which cause ataxia-telangiectasia (A-T), designated ATM, has been purified, isolated and determined.

The present invention further includes the method for identifying carriers of the defective A-T gene and defective A-T gene products.

Further, the present invention provides transgenic and knockout nonhuman animal and cellular models.

The role of the ATM gene in cancer predisposition makes this gene an important target for screening. The detection of A-T mutation carriers is particularly significant in light of their radiation-sensitivity so that carrier exposure to radiation can be properly monitored and avoided.

BRIEF DESCRIPTION OF THE DRAWINGS

Other advantages of the present invention will be readily appreciated as the same becomes better understood by reference to the following detailed description when considered in connection with the accompanying drawings wherein:

FIGS. 1A–E illustrate the positional cloning steps to identify the A-T gene(s) wherein FIG. 1A is a high-density marker map of the A-T region on chromosome 11q22-23 (Vanagaite et al., 1995), constructed by generating microsatellite markers within genomic contigs spanning the region and by physical mapping of available markers using the same contigs, the prefix "D11" has been omitted from the marker designations, FDX: the adrenal ferredoxin gene, ACAT: the acetoacetyl-coenzyme A thiolase gene, the stippled box denotes the A-T interval, defined recently by individual recombinants between the markers S1818 and S1819 in a consortium linkage study (Lange et al., 1995), the solid box indicates the two-lod confidence interval for A-T obtained in that study, between S1294 and S384;

FIG. 1B illustrates a part of a YAC contig constructed across this region (Rotman et al., 1994c);

FIG. 1C illustrates part of a cosmid contig spanning the S384-S1818 interval, generated by screening a chromosome-11 specific cosmid library with YAC clones Y16 and Y67, and subsequent contig assembly of the cosmid clones by physical mapping (Shiloh, 1995);

FIG. 1D illustrates products of gene hunting experiments wherein solid boxes denote cDNA fragments obtained by using cosmid and YAC clones for hybrid selection of cDNAs (Lovett et al. 1991; Tagle et al., 1993) from a variety of tissues, open boxes denote putative exons isolated from these cosmids by exon trapping (Church et al., 1993), these sequences hybridized back to specific cosmids (broken lines), which allowed their physical localization to specific subregions of the contig (dotted frames); and FIG. 1E illustrates a 5.9 kb CDNA clone, designated 7-9, identified in a fibroblast CDNA library using the CDNA fragments and exons in 1D as a probe wherein the open box denotes an open reading frame of 5124 nucleotides, solid lines denote untranslated regions, striped arrowheads denote two Alu elements at the 3' end, and wherein dotted lines drawn between cDNA fragments and exons the CDNA indicate colinearity of sequences.

DETAILED DESCRIPTION OF THE PREFERRED EMBODIMENT

Figure 1:
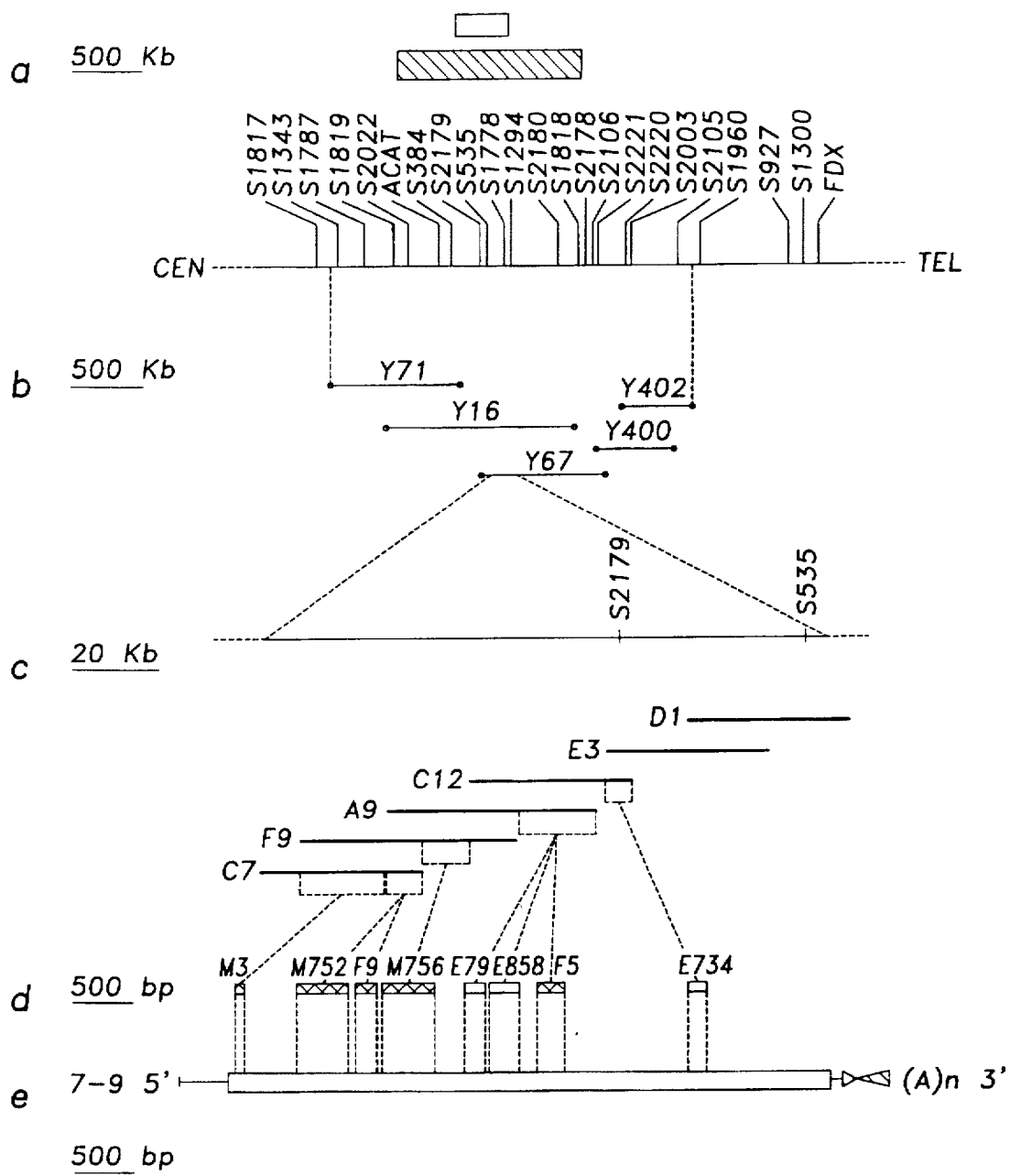

The present invention consists of a purified, isolated and cloned nucleic acid sequence encoding a gene, designated ATM, mutations in which cause ataxia-telangiectasia and genetic polymorphisms thereof. The nucleic acid can be isolated genomic DNA, cDNA or MRNA. A partial sequence of the ATM gene is set forth in SEQ ID No:1 and in SEQ ID No:3 with the more complete sequence set forth in SEQ ID No:9.

SEQ ID No:1 and SEQ ID No:9 include and extend the cDNA sequence of clone 7-9 in the 5' direction as described herein below. Cosmid clones containing the entire 7-9 sequence are described in Savitsky et al. (1995) and incorporated herein by reference.

SEQ ID No:3 is a 6.5 Kb cloned DNA sequence, designated A-T/4 and represents a sequence of DNA which extends the length of SEQ ID No:1 in the 3' direction. SEQ ID No:3 begins at nucleotide 1432 of SEQ ID No:1 and is identical to SEQ ID No:1 through nucleotide 6556 of SEQ ID No:1 which corresponds to nucleotide 5246 of SEQ ID No:3. From nucleotide 5247 of SEQ ID No:3 through its last nucleotide, SEQ ID No:3 differs from SEQ ID No:1. This difference is thought to reflect alternative splicing creating different protein isoforms.

Polymorphisms are variants in the sequence generally found between different ethnic and geographic locations which, while having a different sequence, produce functionally equivalent gene products.

Current mutation data (as shown in Table 1) indicate that A-T is a disease characterized by considerable allelic heterogenicity. It would not be surprising if there were hundreds (or even thousands) of ATM mutations (as is the case for cystic fibrosis and BRACAI). Mutations imparting defects into the A-T gene can be point mutations, deletions, insertions or rearrangements. The mutations can be present within the nucleotide sequence of the either or both alleles of the ATM gene such that the resulting amino acid sequence of the ATM protein product is altered in one or both copies of the gene product; when present in both copies imparting ataxia-telangiectasia. Alternatively, a mutation event selected from the group consisting of point mutations, deletions, insertions and rearrangements could have occurred within the flanking sequences and/or regulatory sequences of ATM such that regulation of ATM is altered imparting ataxia-telangiectasia.

Table 1 illustrates several mutations in the ATM gene found in A-T patients. Mutations in the ATM gene were found in all of the complementation groups suggesting that ATM is the sole gene responsible for all A-T cases.

1992; Tagle et al., 1993). In parallel experiments, YAC clones were bound to a solid matrix and used to select cDNA fragments from a heterogeneous cDNA collection representing several human tissues (Parimoo et al., 1993). The

TABLE 1 illustrates several mutations found in A-T patients

| Patient[1] | Ethnic/ geographic origin | Complementation group[4] | Mutation mRNA sequence change | Protein alteration | Codon[9] | Patient's genotype[10] |
|---|---|---|---|---|---|---|
| AT2RO | Arab | A | Deletion of 11 nt[5] | Frameshift, truncation | 499 | Homozygote |
| AT3NG | Dutch | A | Deletion of 3 nt | Deletion, 1 residue[8] | 1512 | Compound heterozygote |
| AT15LA | Philippine | A | Insertion, +A | Frameshift, truncation | 557 | Compound heterozygote |
| AT3LA[2] AT4LA[2] | African-American | C | Deletion of 139 nt[6]/ Deletion of 298 nt[6] | Frameshift, trunction | 1196 | Compound heterozygotes |
| AT2BR | Celtic/Irish | C | Deletion, 9 nt | Deletion, 3 residues | 1198–1200 | Homozygote |
| AT1ABR AT2ABR | Australian (Irish/British) | E | Deletion, 9 nt | Deletion, 3 residues | 1198–1200 | Homozygote |
| AT5BI[2] AT6BI[2] | Indian/English | D | Deletion, 6 nt | Deletion, 2 residues | 1079–1080 | Compound heterozygotes |
| F-2079[3] | Turkish | ND | Insertion, +C[5] | Frameshift, truncation | 504 | Homozygote |
| AT29RM | Italian | ND | Deletion of 175 nt | Frameshift, truncation | 132 | Homozygote |
| AT103LO | Canadian | ND | Insertion, +A | Frameshift, truncation | 1635 | Homozygote |
| F-596[3] | Palestinian Arab | ND | Deletion[7] | Truncation | Most of ORF | Homozygote |

[1]Cell line designation.
[2]Sibling patients in both of whom the same mutation was identified.
[3]Patient expected to be homozygous by descent for an A-T mutation.
[4]According to the methods of Jaspers et al. (1988) ND: not determined.
[5]An identical sequence change was observed in genomic DNA
[6]No evidence for deletion was observed in genomic DNA. In both siblings, a normal mRNA was observed in addition to the two deleted species. The two deleted mRNAs may represent abnormal splicing events caused by a splice site mutation.
[7]Reflects a genomic deletion segregating with the disease in Family N.
[8]The deleted serine residue is located within the PI3-kinase signature sequence (1507–1527 of SEQ ID No:2).
[9]Numbers refer to residue positions in SEQ ID No:2.
[10]In all the compound heterozygotes, the second mutation is still unidentified.

In cloning the gene for A-T, the strategy used was a common strategy in identifying a disease gene with an unknown protein product known as positional cloning, as is well known in the art. In positional cloning, the target gene is localized to a specific chromosomal region by establishing linkage between the disease and random genetic markers defined by DNA polymorphisms. Definition of the smallest search interval for the gene by genetic analysis is followed by long-range genomic cloning and identification of transcribed sequences within the interval. The disease gene is then identified among these sequences, mainly by searching for mutations in patients.

Several important and long sought disease genes were isolated recently in this way (Collins, 1992; Attree et al., 1992; Berger et al., 1992; Chelly et al., 1993; Vetrie et al., 1993; Trofatter et al., 1993; The Huntington's Disease Collaborative Research Group, 1993; The European Polycystic Kidney Disease Consortium, 1994; Miki et al., 1994).

Two complementary methods were used for the identification of transcribed sequences (gene hunting): hybrid selection based on direct hybridization of genomic DNA with cDNAs from various sources (Parimoo et al., 1991; Lovett et al., 1991); and exon trapping (also called exon amplification), which identifies putative exons in genomic DNA by virtue of their splicing capacity (Church et al., 1993). In hybrid selection experiments, cosmid and YAC clones served to capture cross-hybridizing sequences in cDNA collections from placenta, thymus and fetal brain, using the magnetic bead capture protocol (Morgan et al., cosmids were also used for exon trapping with the pSPL3 vector (Church et al., 1994). The captured cDNA fragments and trapped exons were mapped back to the A-T region by hybridization to several radiation hybrids containing various portions of the 11q22-23 region (Richard et al., 1993; James et al., 1994), and to high-density grids containing all the YACs and cosmids spanning this interval. An extensive transcriptional map of the A-T region was thus constructed (Shiloh et al., 1994).

Pools of adjacent cDNA fragments and exons, expected to converge into the same transcriptional units, were used to screen cDNA libraries. A cluster of 5 cDNA fragments and 3 exons mapped in close proximity to the marker D11S535, where the location score for A-T had peaked (Lange et al., 1995). All these sequences hybridized to the same 5.9 kb of the CDNA clone, 7-9, obtained from a fibroblast CDNA library.

Hybridization of the 7-9 CDNA clone to the radiation hybrid panel indicated that the entire transcript was derived from the chromosome 11 locus. The full sequence of this clone was obtained using a shotgun strategy, and found to contain 5921 bp which includes an open reading frame (ORF) of 5124 nucleotides, a 538 bp 3' untranslated region (3' UTR), and a 259 bp 5' non-coding sequence containing stop codons in all reading frames. (Genbank Accession No. U26455). Two Alu repetitive elements were observed at the 3' end of this clone and in nine smaller clones representing this gene from the same cDNA library. Since no polyadenylation signal was identified in these CDNA clones, their poly(A) tracts were assumed to be associated with the Alu element rather than being authentic poly(A) tails of these transcripts. This assumption was later supported when applicants identified a cDNA clone derived from the same gene in a leukocyte cDNA library, with an alternative 3' UTR containing a typical polyadenylation signal. Alignment of the cDNA with the genomic physical map showed that the corresponding gene is transcribed from centromere to telomere.

Hybridization of a probe containing the entire ORF of clone 7-9 to northern blots from various tissues and cell lines revealed a major transcript of 12 kb in all tissues and cell types examined, and minor species of various sizes in several tissues, possibly representing alternatively spliced transcripts of the corresponding gene or other homologous sequences. Analysis of 12 additional cDNA clones corresponding to this gene indicated a plethora of transcripts generated by multiple alternative splicing combinations. Genomic sequencing later identified the 5' non-coding region of clone 7-9 as sequences of the unspliced adjacent intron. Two other CDNA clones from a leukocyte cDNA library were found to contain this intronic sequence in their 5' ends. These clones may represent either splicing intermediates, or alternatively spliced transcripts of this gene, in which sequences of the adjacent intron were left to serve as an untranslated leader.

The invention further provides a purified protein as encoded by the ATM gene and analogs thereof. A consensus sequence is set forth in SEQ ID No:2 with the complete sequence set forth in SEQ ID No:8. The present invention further provides for mutations in SEQ ID No:2 and SEQ ID No:8 which cause ataxia-telangiectasia, for example, as set forth in Table 1.

The present invention further includes a recombinant protein encoded by the 7-9 clone and/or by SEQ ID No:8. This recombinant protein is isolated and purified by techniques known to those skilled in the art.

An analog will be generally at least 70% homologous over any portion that is functionally relevant. In more preferred embodiments, the homology will be at least 80% and can approach 95% homology to the ATM protein. The amino acid sequence of an analog may differ from that of the ATM protein when at least one residue is deleted, inserted or substituted but the protein remains functional and does not cause A-T. Differences in glycosylation can provide analogs.

The present invention provides an antibody, either polyclonal or monoclonal, which specifically binds to a polypeptide/protein encoded by the ATM gene. In preparing the antibody, the protein (with and without mutations) encoded by the ATM gene and polymorphisms thereof is used as a source of the immunogen. Alternatively, the consensus protein set forth in SEQ ID No:2 or the complete sequence set forth in SEQ ID No:8 can be used. Peptide amino acid sequences isolated from the amino acid sequence as set forth in SEQ ID No:2 and SEQ ID No:8 or mutant peptide sequences can also be used as an immunogen.

The present invention specifically provides antibodies against the following peptides:

HEPANSSASQSTDLC (SEQ ID No:4),

CKRNLSDIDQSFDKV (SEQ ID No:5),

PEDETELHPTLNADDQEC (SEQ ID No:6), and

CKSLASFIKKPFDRGEVESMEDDTNG (SEQ ID No:7).

The antibodies may be either monoclonal or polyclonal. Conveniently, the antibodies may be prepared against a synthetic peptide based on the sequence, or prepared recombinantly by cloning techniques or the natural gene product and/or portions thereof may be isolated and used as the immunogen. Such proteins or peptides can be used to produce antibodies by standard antibody production technology well known to those skilled in the art as described generally in Harlow and Lane, Antibodies: A Laboratory Manual, Cold Spring Harbor Laboratory Press, Cold Spring Harbor, N.Y., 1988.

For producing polyclonal antibodies a host, such as a rabbit or goat, is immunized with the protein or peptide, generally with an adjuvant and, if necessary, coupled to a carrier; antibodies to the protein are collected from the sera.

For producing monoclonal antibodies, the technique involves hyperimmunization of an appropriate donor, generally a mouse, with the protein or peptide fragment and isolation of splenic antibody producing cells. These cells are fused to a cell having immortality, such as a myeloma cell, to provide a fused cell hybrid which has immortality and secretes the required antibody. The cells are then cultured, in bulk, and the monoclonal antibodies harvested from the culture media for use.

The antibody can be bound to a solid support substrate or conjugated with a detectable moiety or be both bound and conjugated as is well known in the art. (For a general discussion of conjugation of fluorescent or enzymatic moieties see Johnstone and Thorpe, Immunochemistry in Practice, Blackwell Scientific Publications, Oxford, 1982.) The binding of antibodies to a solid support substrate is also well known in the art. (see for a general discussion Harlow and Lane Antibodies: A Laboratory Manual, Cold Spring Harbor Laboratory Publications, New York, 1988) The detectable moieties contemplated with the present invention can include, but are not limited to, fluorescent, metallic, enzymatic and radioactive markers such as biotin, gold, ferritin, alkaline phosphatase, β-galactosidase, peroxidase, urease, fluorescein, rhodamine, tritium, $^{14}C$ and iodination.

The present invention provides vectors comprising an expression control sequence operatively linked to the nucleic acid sequence of the ATM gene, SEQ ID No:9 as well as SEQ ID No:1 and SEQ ID No:3 and portions thereof as well as mutant sequences which lead to the expression of A-T. The present invention further provides host cells, selected from suitable eucaryotic and procaryotic cells, which are transformed with these vectors.

Using the present invention, it is possible to transform host cells, including E. coli, using the appropriate vectors so that they carry either the native or recombinant DNA sequence of the 7-9 cDNA clone or a mutated sequence containing point mutations, deletions, insertions, or rearrangements of DNA as well as the ATM gene, SEQ ID No:9, as well as SEQ ID No:1 and SEQ ID No:3 and portions thereof with mutant sequences which lead to the expression of A-T. Such transformed cells allow the study of the function and the regulation of the A-T gene. Use of recombinantly transformed host cells allows for the study of the mechanisms of A-T and, in particular it will allow for the study of gene function interrupted by the mutations in the A-T gene region.

Vectors are known or can be constructed by those skilled in the art and should contain all expression elements necessary to achieve the desired transcription of the sequences. Other beneficial characteristics can also be contained within the vectors such as mechanisms for recovery of the nucleic acids in a different form. Phagemids are a specific example of such beneficial vectors because they can be used either as plasmids or as bacteriophage vectors. Examples of other vectors include viruses such as bacteriophages, baculoviruses and retroviruses. DNA viruses, cosmids, plasmids, liposomes and other recombination vectors. The vectors can also contain elements for use in either procaryotic or eucaryotic host systems. One of ordinary skill in the art will know which host systems are compatible with a particular vector.

The vectors can be introduced into cells or tissues by any one of a variety of known methods within the art. Such methods can be found generally described in Sambrook et al., *Molecular Cloning: A Laboratory Manual*, Cold Springs Harbor Laboratory, New York (1992), in Ausubel et al., *Current Protocols in Molecular Biology*, John Wiley and Sons, Baltimore, Md. (1989), Chang et al., *Somatic Gene Therapy*, CRC Press, Ann Arbor, Mich. (1995), Vega et al., *Gene Targeting*, CRC Press, Ann Arbor, Mich. (1995) and Gilboa et al (1986) and include, for example, stable or transient transfection, lipofection, electroporation and infection with recombinant viral vectors. Introduction of nucleic acids by infection offers several advantages over the other listed methods. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

Recombinant methods known in the art can also be used to achieve the sense, antisense or triplex inhibition of a target nucleic acid. For example, vectors containing antisense nucleic acids can be employed to express protein or antisense message to reduce the expression of the target nucleic acid and therefore its activity.

A specific example of DNA viral vector for introducing and expressing antisense nucleic acids is the adenovirus derived vector Adenop53TK. This vector expresses a herpes virus thymidine kinase (TK) gene for either positive or negative selection and an expression cassette for desired recombinant sequences such as antisense sequences. This vector can be used to infect cells that have an adenovirus receptor which includes most cancers of epithelial origin as well as others. This vector as well as others that exhibit similar desired functions can be used to treat a mixed population of cells include, for example, an in vitro or ex vivo culture of cells, a tissue or a human subject.

Additional features can be added to the vector to ensure its safety and/or enhance its therapeutic efficacy. Such features include, for example, markers that can be used to negatively select against cells infected with the recombinant virus. An example of such a negative selection marker is the TK gene described above that confers sensitivity to the anti-viral gancyclovir. Negative selection is therefore a means by which infection can be controlled because it provides inducible suicide through the addition of antibiotic. Such protection ensures that if, for example, mutations arise that produce altered forms of the viral vector or sequence, cellular transformation will not occur. Features that limit expression to particular cell types can also be included. Such features include, for example, promoter and regulatory elements that are specific for the desired cell type.

Recombinant viral vectors are another example of vectors useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. The vector to be used in the methods of the invention will depend on desired cell type to be targeted. For example, if breast cancer is to be treated, then a vector specific for such epithelial cells should be used. Likewise, if diseases or pathological conditions of the hematopoietic system are to be treated, then a viral vector that is specific for blood cells and their precursors, preferably for the specific type of hematopoietic cell, should be used.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed will not contain a genome and therefore cannot proceed through subsequent rounds of infection. The specific type of vector will depend upon the intended application. The actual vectors are also known and readily available within the art or can be constructed by one skilled in the art using well-known methodology.

If viral vectors are used, for example, the procedure can take advantage of their target specificity and consequently, do not have to be administered locally at the diseased site. However, local administration may provide a quicker and more effective treatment, administration can also be performed by, for example, intravenous or subcutaneous injection into the subject. Injection of the viral vectors into a spinal fluid can also be used as a mode of administration, especially in the case of neuro-degenerative diseases. Following injection, the viral vectors will circulate until they recognize host cells with the appropriate target specificity for infection.

Transfection vehicles such as liposomes can also be used to introduce the non-viral vectors described above into recipient cells within the inoculated area. Such transfection vehicles are known by one skilled within the art.

The present invention includes the construction of transgenic and knockout organisms that exhibit the phenotypic manifestations of A-T. The present invention provides for transgenic ATM gene and mutant ATM gene animal and cellular (cell lines) models as well as knockout ATM models. The transgenic models include those carrying the sequence set forth SEQ ID No:9, or at least, SEQ ID No:1 and/or SEQ ID No:3. These models are constructed using standard methods known in the art and as set forth in U.S. Pat. Nos. 5,387,742, 5,360,735, 5,347,075, 5,298,422, 5,288,846, 5,221,778, 5,175,385, 5,175,384, 5,175,383, 4,736,866 as well as Burke and Olson, (1991), Capecchi, (1989), Davies et al., (1992), Dickinson et al., (1993), Huxley et al., (1991), Jakobovits et al., (1993), Lamb et al., (1993), Rothstein, (1991), Schedl et al., (1993), Strauss et al., (1993). Further, patent applications WO 94/23049, WO 93/14200, WO 94/06908, WO 94/28123 also provide information. See also in general Hogan et al "Manipulating the Mouse Embryo" Cold Spring Harbor Laboratory Press, 2nd Edition (1994).

According to the present invention, there is provided a method for diagnosing and detecting carriers of the defective gene responsible for causing A-T. The present invention further provides methods for detecting normal copies of the ATM gene and its gene product. Carrier detection is especially important since A-T mutations underlie certain cases of cancer predisposition in the general population. Identifying the carriers either by their defective gene or by their missing or defective protein(s) encoded thereby, leads to earlier and more consistent diagnosis of A-T gene carriers. Thus, since carriers of the disease are more likely to be cancer-prone and/or sensitive to therapeutic applications of radiation, better surveillance and treatment protocols can be initiated for them. Conversely, exclusion of A-T heterozygotes from patients undergoing radiotherapy can allow for establishing routinely higher dose schedules for other cancer patients thereby improving the efficacy of their treatment.

Briefly, the methods comprise the steps of obtaining a sample from a test subject, isolating the appropriate test material from the sample and assaying for the target nucleic acid sequence or gene product. The sample can be tissue or bodily fluids from which genetic material and/or proteins are isolated using methods standard in the art. For example, DNA can be isolated from lymphocytes, cells in amniotic fluid and chorionic villi (Llerena et al., 1989).

More specifically, the method of carrier detection is carried out by first obtaining a sample of either cells or bodily fluid from a subject. Convenient methods for obtaining a cellular sample can include collection of either mouth wash fluids or hair roots. A cell sample could be amniotic or placental cells or tissue in the case of a prenatal diagnosis. A crude DNA could be made from the cells (or alternatively proteins isolated) by techniques well known in the art. This isolated target DNA is then used for PCR analysis (or alternatively, Western blot analysis for proteins) with appropriate primers derived from the gene sequence by techniques well known in the art. The PCR product would then be tested for the presence of appropriate sequence variations in order to assess genotypic A-T status of the subject.

The specimen can be assayed for polypeptides/proteins by immunohistochemical and immunocytochemical staining (see generally Stites and Terr, *Basic and Clinical Immunology*, Appleton and Lange, 1994), ELISA, RIA, immunoblots, Western blotting, immunoprecipitation, functional assays and protein truncation test. In preferred embodiments, Western blotting, functional assays and protein truncation test (Hogervorst et al., 1995) will be used. mRNA complementary to the target nucleic acid sequence can be assayed by in situ hybridization, Northern blotting and reverse transcriptase—polymerase chain reaction. Nucleic acid sequences can be identified by in situ hybridization, Southern blotting, single strand conformational polymorphism, PCR amplification and DNA-chip analysis using specific primers. (Kawasaki, 1990; Sambrook, 1992; Lichter et al, 1990; Orita et al, 1989; Fodor et al., 1993; Pease et al., 1994)

ELISA assays are well known to those skilled in the art. Both polyclonal and monoclonal antibodies can be used in the assays. Where appropriate other immunoassays, such as radioimmunoassays (RIA) can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, 1992.

Current mutation data (as shown in Table 1) indicate that A-T is a disease characterized by considerable allelic heterogenicity. It would not be surprising if there were hundreds (or even thousands) of ATM mutations (as is the case for cystic fibrosis and BRACAI). Thus, it will be important for a successful mutation screen to be able to detect all possible nucleotide alterations in the ATM gene, rather than being focused on a limited subset. Methods including direct sequencing of PCR amplified DNA or RNA or DNA chip hybridization (Fodor et al., 1993; Pease et al., 1994) can be applied along with other suitable methods known to those skilled in the art.

In order to use the method of the present invention for diagnostic applications, it is advantageous to include a mechanism for identifying the presence or absence of target polynucleotide sequence (or alternatively proteins). In many hybridization based diagnostic or experimental procedures, a label or tag is used to detect or visualize for the presence or absence of a particular polynucleotide sequence. Typically, oligomer probes are labelled with radioisotopes such as $^{32}$p or $^{35}$S (Sambrook, 1992) which can be detected by methods well known in the art such as autoradiography. Oligomer probes can also be labelled by non-radioactive methods such as chemilluminescent materials which can be detected by autoradiography (Sambrook, 1992). Also, enzyme-substrate based labelling and detection methods can be used. Labelling can be accomplished by mechanisms well known in the art such as end labelling (Sambrook, 1992), chemical labelling, or by hybridization with another labelled oligonucleotide. These methods of labelling and detection are provided merely as examples and are not meant to provide a complete and exhaustive list of all the methods known in the art.

The introduction of a label for detection purposes can be accomplished by attaching the label to the probe prior to hybridization.

An alternative method for practicing the method of the present invention includes the step of binding the target DNA to a solid support prior to the application of the probe. The solid support can be any material capable of binding the target DNA, such as beads or a membranous material such as nitrocellulose or nylon. After the target DNA is bound to the solid support, the probe oligomers is applied.

Functional assays can be used for detection of A-T carriers or affected individuals. For example, if the ATM protein product is shown to have PI 3-kinase biochemical activity which can be assayed in an accessible biological material, such as serum, peripheral leukocytes, etc., then homozygous normal individuals would have approximately normal biological activity and serve as the positive control. A-T carriers would have substantially less than normal biological activity, and affected (i.e. homozygous) individuals would have even less biological activity and serve as a negative control. Such a biochemical assay currently serves as the basis for Tay-Sachs carrier detection.

The present invention also provides a kit for diagnosis and detection of the defective A-T gene. The kit includes a molecular probe complimentary to genetic sequences of the defective gene which causes ataxia-telangiectasia (A-T) andsuitable labels for detecting hybridization of the molecular probe and the defective gene thereby indicating the presence of the defective gene. The molecular probe has a DNA sequence complementary to mutant sequences. Alternatively, the kit can contain reagents and antibodies for detection of mutant proteins.

The above discussion provides a factual basis for the use and identification of the ataxia-telangiectasia gene and gene products and identification of carriers as well as construction of transgenic organisms. The methods used in the present invention can be shown by the following non-limiting example and accompaning figures.

EXAMPLE

Materials and Methods

General Methods in Molecular Biology

Standard molecular biology techniques known in the art and not specifically described were generally followed as in Sambrook et al., *Molecular Cloning: A Laboratory Manual*, Cold Springs Harbor Laboratory, New York (1989, 1992), and in Ausubel et al., *Current Protocols in Molecular Biology*, John Wiley and Sons, Baltimore, Md. (1989).

Patient and Family Resources

A cell line repository was established containing 230 patient cell lines and 143 cell lines from healthy members of Moroccan Jewish, Palestinian Arab and Druze families. Some of these pedigrees are highly inbred and unusually large (Ziv et al., 1991; Ziv, 1992). In view of the large number of meiotic events required for high-resolution linkage analysis, applicants collaborated with Dr. Carmel McConville (University of Birmingham, UK) and Dr. Richard Gatti (UCLA, Los Angeles, Calif.), who have also established extensive repositories of A-T families. Linkage analysis was conducted on a pool of 176 families.

Definition of the A-T Interval by Genetic Analysis

Studies based only on analysis of Israeli A-T families enabled localization of the A-T(C) gene at 11q22-23 (Ziv, 1991), and confirmed the localization of A-T(A) mutation in Palestinians to the same region (Ziv et al., 1992). Studies with the Birmingham group further narrowed the major A-T interval to 4 centimorgans, between D11S611 and D11S1897 (McConville et al., 1993), and subsequently to 3 centimorgans, between GRIA4 and D11S1897 (Ambrose et al., 1994; McConville et al., 1994) (see also Shiloh, 1995, and FIG. 1).

All these studies were conducted with biallelic markers, whose power is limited by their low polymorphic information content (PIC). The recently discovered microsatellite markers based on variable numbers of tandem simple repeats (Litt and Luty, 1989; Weber and May, 1989) are much more powerful due to their high degree of polymorphism. Microsatellite markers were used to saturate the A-T region using two approaches. The first, was based on physical mapping of microsatellite markers generated by others which were loosely linked to chromosome 11q.

Mapping experiments were conducted using YAC and cosmid contigs which allowed precise, high-resolution localization of DNA sequences in this region of chromosome 11. These experiments led to the localization of 12 microsatellites at the A-T region (Vanagaite et al., 1994a; Vanagaite et al., 1995).

The second approach was based on generating new microsatellites within the YAC contig. A rapid method for the identification of polymorphic CA-repeats in YAC clones was set up (Rotman, 1995) resulting in the generation of twelve new markers within the A-T locus (Vanagaite et al., 1995; Rotman et al., 1995; Rotman et al., 1994b). Hence, the high-density microsatellite map constructed in this manner contained a total of 24 new microsatellite markers and spans the A-T locus and flanking sequences, over a total of six megabases (Vanagaite et al., 1995).

Repeated linkage analysis on the entire cohort of A-T families indicated that the A-T(A) locus was definitely located within a 1.5 megabase region between D11S1819 and D11S1818 (Gatti et al., 1994) as shown in FIG. 1 and in Shiloh (1995), with a clear peak of the cumulative lod score under D11S535 (Lange et al., 1994).

Concomitant with these studies, linkage disequilibrium (LD) analysis of Moroccan-Jewish A-T patients was conducted. LD refers to the non-random association between alleles at two or more polymorphic loci (Chakravarti et al., 1984). LD between disease loci and linked markers is a useful tool for the fine localization of disease genes (Chakravarti et al., 1984; Kerem et al. 1989; Ozelius et al., 1992; Sirugo et al., 1992; Hastbacka et al., 1992; Mitchison et al., 1993). LD is particularly powerful in isolated ethnic groups, where the number of different mutations at a disease locus is likely to be low (Hastbacka et al., 1992; Lehesjoki et al., 1993; Aksentijevitch et al., 1993). Early on, applicants observed very significant LD (p<0.02–p<0.001) between A-T and markers along the D11S1817–D11S927 region in the patients of the sixteen Moroccan-Jewish A-T families identified in Israel (Oskato et al., 1993). Further analysis with the new markers narrowed the peak of linkage disequilibrium to the D11S384-D11S1818 region as shown in FIG. 1.

Haplotype analysis indicated that all of the mutant chromosomes carry the same D11S384–D11S1818 haplotype, suggesting a founder effect for A-T in this community, with one mutation predominating.

Long-range Cloning of the A-T(A)/A-T(C) Region

Cloning the disease locus in a contig (set of overlapping clones) was essential in isolating the A-T disease gene. The entire A-T locus and flanking region in a contig of yeast artificial chromosomes (YACs) was cloned by methods well known in the art (Rotman et al. 1994c; Rotman et al., 1994d). This contig was instrumental in the construction of the microsatellite map of the region (Vanagaite et al., 1995) and subsequently enabled construction of cosmid contigs extending over most of the interval D11S384-D11S1818. Cosmids corresponding to the YAC clones were identified in a chromosome 11-specific cosmid library supplied by Dr. L. Deaven (Los Alamos National Laboratory) and were ordered into contigs by identifying overlaps as shown in FIG. 1.

Isolation of the A-T gene

Transcribed sequences were systematically identified based on two complementary methods:

1. Use of an improved direct selection method based on magnetic bead capture (MBC) of cDNAs corresponding to genomic clones (Morgan et al., 1992; Tagle et al., 1993). In several, large-scale experiments YAC or cosmid DNA was biotinylated and hybridized to PCR-amplified cDNA from thymus, brain and placenta. Genomic DNA-cDNA complexes were captured using streptavidin-coated magnetic beads which was followed with subsequent elution, amplification, and cloning of captured cDNAs. The cDNA inserts were excised from a gel, self-ligated to form concatamers and sonicated to obtain random fragments. These fragments were size fractionated by gel electrophoresis, and the 1.0–1.5 Kb fraction was extracted from the gel and subcloned in a plasmid vector. The end portions of individual clones were sequenced using vector-specific primers, in an automated sequencer (Model 373A, Applied Biosystems), and the sequences were aligned using the AutoAssembler program (Applied Biosystems Division, Perkin-Elmer Corporation). In the final sequence each nucleotide position represents at least 3 independent overlapping readings.

YACs were also used and were no less efficient than cosmids as starting material for MBC, with more than 50% of the products mapping back to the genomic clones. However, when a small panel of radiation hybrids spanning the A-T region was used to test the CDNA fragments, it was found that some clones that hybridized back to the YACs and cosmids were not derived from this region. This pitfall probably stems from limited homology between certain portions of different genes, and points up the necessity to use radiation hybrid mapping when testing the authenticity of the captured sequences, and not to rely solely on cloned DNA for this purpose.

Homology searches in sequence databases showed that only one of the first 105 CDNA fragments mapped to the A-T region was homologous to a sequence previously deposited in one of the databases, as an expressed sequence tag (EST). 2. Exon amplification, also termed "exon trapping" (Duyk et al., 1990; Buckler et al., 1991), is based on cloning genomic fragments into a vector in which exon splice sites are flagged by splicing to their counterpart sites in the vector. This method of gene identification was expected to complement the MBC strategy, since it does not depend on the constitution of cDNA libraries or on the relative abundance of transcripts, and is not affected by the presence of repetitive sequences in the genomic clones. An improved version of this system (Church et al., 1993) that eliminated problems identified in an earlier version, including a high percentage of false positives and the effect of cryptic splice sites was utilized. Each experiment ran a pool of three to five cosmids with an average of two to five exons identified per cosmid. A total of forty five exons were identified.

Sequence analysis and physical mapping indicated that MBC and exon amplification were complementary in identifying transcribed sequences.

The availability of a deep cosmid contig enabled rapid and precise physical localization of the cDNA fragments and captured exons, leading to a detailed transcriptional map of the A-T region.

Both MBC and exon amplification yielded short (100–1000 bp) transcribed sequences. Those sequences were used as anchor points in isolating full-length clones from twenty eight cDNA libraries currently at applicants disposal and which represented a variety of tissues and cell lines.

Initial screening of the cDNA libraries by polymerase chain reaction (PCR) using primer sets derived from individual cDNA fragments or exons aided in the identification of the libraries most likely to yield corresponding cDNA clones.

Large scale screening experiments were carried out in which most of the cDNA fragments and exons were used in large pools. In addition to the mass screening by hybridization, PCR-based screening methods and RACE (rapid amplification of cDNA ends) (Frohman et al., 1988; Frohman et al., 1994) was employed to identify full-length cDNAs.

The above experiments resulted in the identification and isolation of a cDNA clone designated 7-9, the sequence of which is included in SEQ ID No:1 (and SEQ ID No:9), and which is derived from a gene located under the peak of cumulative location score obtained by linkage analysis as shown in FIG. 1. The gene extends over some 300 kilobases (kb) of genomic DNA and codes for two major MRNA species of 12 kb and 10.5 kb in length. The 7-9 clone is 5.9 kb in length and, therefore, is not a full length clone.

An open reading frame of 5124 bp within this cDNA encodes a protein with signature motifs typical of signal transduction proteins, most notably, phosphatidylinositol 3-kinases (PI 3-kinases). PI 3-kinases take part in the complex system responsible for transmitting signals from the outer environment of a cell into the cell. To date, it is not clear whether the protein produced from the 7-9 clone is a part of this transduction system or if it merely contains sequence motifs typical to signal transduction proteins.

Throughout this application various publications and patents are referenced by citation or number. Full citations for the publications referenced are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

Aksentijevitch et al., "Familial Mediterranean fever in Moroccan Jews: Demonstration of a founder effect by extended haplotype analysis" Am. J. Hum. Genet., 53:644–651 (1993).

Ambrose et al., "A physical map across chromosome 11q22-23 containing the major locus for ataxia-telangiectasia. Genomics, 21:612–619 (1994).

Attree et al., "The Lowe's oculocerebrorenal syndrome gene encodes protein highly homologous to inositol polyphosphate-5-phosphatase" Nature, 358:239–242 (1992).

Barker, "A more robust, rapid alkaline denaturation sequencing method", BioTechniques, Vol. 14, No. 2, pp. 168–169 (1993).

Berger et al., "Isolation of a candidate gene for Norrie disease by positional cloning" Nature Genet. 1:199–203, (1992)

Buckler et al., "Exon amplification: a strategy to isolate mammalian genes based on RNA splicing" Proc. Natl. Acad. Sci. USA, 88:4005–4009 (1991).

Burke and Olson, "Preparation of Clone Libraries in Yeast Artificial-Chromosome Vectors" in Methods in Enzymology, Vol. 194, "Guide to Yeast Genetics and Molecular Biology", eds. C. Guthrie and G. Fink, Academic Press, Inc., Chap. 17, pp. 251-270 (1991).

Capecchi, "Altering the genome by homologous recombination" Science 244:1288–1292 (1989).

Chakravarti et al., "Nonuniform recombination within the human beta-globin gene cluster" Am. J. Hum. Genet., 36:1239–1258 (1984).

Chelly et al., "Isolation of a candidate gene for Menkes disease that encodes a potential heavy metal binding protein" *Nature Genet.* 3:14–19 (1993).

Church et al., "Isolation of genes from complex sources of mammalian genomic DNA using exon amplification" *Nature Genet.* 6:98–104 (1993).

Collins, F. S. "Positional cloning: let's not call it reverse anymore" *Nature Genet.*, 1:3–6 (1992).

Davies et al., "Targeted alterations in yeast artificial chromosomes for inter-species gene transfer", *Nucleic Acids Research*, Vol. 20, No. 11, pp. 2693–2698 (1992).

Dickinson et al., "High frequency gene targeting using insertional vectors", *Human Molecular Genetics*, Vol. 2, No. 8, pp. 1299–1302 (1993).

Duyk et al., "Exon trapping: A genetic screen to identify candidate transcribed sequences in cloned mammalian genomic DNA" *Proc. Natl. Acad. Sci. USA*, 87:8995–8999 (1990).

Fodor et al, "Multiplexed biochemical assays with biological chips", *Nature* 364:555–556 (1993)

Foroud et al. "Localization of the AT locus to an 8 cM interval defined by STMY and S132" *Am. J. Hum. Genet.*, 49:1263–1279 (1991).

Frohman, M. A. "On beyond classic RACE (rapid amplification of cDNA ends)" *PCR Methods and Applications*, 4:S40–S58 (1994).

Frohman et al., "Rapid production of full-length cDNAs from rare transcripts: Amplification using a single gene-specific oligonucleotide primer" *Proc. Natl. Acad. Sci. USA*, 85:8998–9002 (1988).

Gatti et al., "Genetic haplotyping of ataxia-telangiectasia families localizes the major gene to an 850 kb region on chromosome 11q23.1" *Int. J. Radiat. Biol.* (1994).

Gatti et al. "Localization of an ataxia-telangiectasia gene to chromosome 11q22-23" *Nature*, 336: 577–580 (1988).

Gilboa et al. "Transfer and expression of cloned genes using retroviral vectors" *BioTechniques* 4(6):504–512 (1986).

Hastbacka et al., "Linkage disequilibrium mapping in isolated founder populations: diastrophic dysplasia in Finland" *Nature Genet.*, 2:204–211 (1992).

Hogervorst et al., "Rapid detection of BRCA1 mutations by the protein truncation test" *Nature Genetics* 10:208–212 (1995).

Huxley et al., "The human HPRT gene on a yeast artificial chromosome is functional when transferred to mouse cells by cell fusion", *Genomics*, 9:742–750 (1991).

Jakobovits et al., "Germ-line transmission and expression of a human-derived yeast artificial chromosome", *Nature*, Vol. 362, pp. 255–261 (1993).

James et al., *Nature Genet.* 8:70 (1994).

Jaspers et al., *Cytogenet. Cell Genet.*, 49:259 (1988).

Kawasaki ES. Amplification of RNA. In: PCR protocols: A Guide to Methods and Applications, Innis M A, Gelfand D H, Sninsky J J, White T J, eds. Academic Press, 1990, pp21–27.

Kerem et al., "Identification of the cystic fibrosis gene: genetic analysis" *Science*, 245:1073–1080 (1989).

Lamb et al., "Introduction and expression of the 400 kilobase precursor amyloid protein gene in transgenic mice", *Nature Genetics*, Vol. 5, pp. 22–29 (1993).

Lange et al., "Localization of an ataxia-telangiectasia gene to a 850 kb interval on chromosome 11q23.1 by linkage analysis of 176 families in an international consortium" *Am. J. Hum. Genet.* (1995).

Lehesjoki et al., "Localization of the EPM1 gene for progressive myoclonus epilepsy on chromosome 21: linkage disequilibrium allows high resolution mapping" *Hum. Mol. Genet.*, 2:1229–1234 (1993).

Lichter et al., "High-resolution mapping of human chromosome 11 by in situ hybridization with cosmid clones" *Science* 247:64–69 (1990).

Litt and Luty, "A hypervariable microsatellite revealed by in vitro amplification of a dinucleotide repeat within the cardiac muscle actin gene" *Am. J. Hum. Genet.*, 44:397–401 (1989).

Llerena et al., "Spontaneous and induced chromosome breakage in chorionic villus samples: a cytogenetic approach to first trimester prenatal diagnosis of ataxia-telangiectasia syndrome" *J. Med. Genet.*, 26:174–178 (1989).

Lovett et al., *Proc. Natl. Acad. Sci. USA* 88, 9628 (1991)

McConville et al., "Genetic and physical mapping of the ataxia-telangiectasia locus on chromosome 11q22-23" *Int. J. Radiat. Biol.* (1994).

McConville et al., "Paired STSs amplified from radiation hybrids, and from associated YACs, identify highly polymorphic loci flanking the ataxia-telangiectasia locus on chromosome 11q22-23" *Hum. Mol. Genet.*, 2:969–974 (1993).

McConville et al., "Fine mapping of the chromosome 11q22-23 region using PFGE, linkage and haplotype analysis; localization of the gene for ataxia telangiectasia to a 5cM region flanked by NCAM/DRD2 and STMY/CJ52.75, phi2.22" *Nucleic Acids Res.*, 18:4335–4343 (1990).

Miki et al. "A strong candidate for the breast and ovarian cancer susceptibility gene BRCA1" *Science*, 266:66–71 (1994).

Mitchison et al., "Fine genetic mapping of the Batten Disease locus (CLN3) by haplotype analysis and demonstration of allelic association with chromosome 16p microsatellite loci" *Genomics*, 16:455–460 (1993).

Morgan et al., "The selective isolation of novel cDNAs encoded by the regions surrounding the human interleukin 4 and 5 genes" *Nucleic Acids Res.*, 20:5173–5179 (1992).

Orita et al. Detection of polymorphisms of human DNA by gel electrophoresis as single-strand conformation polymorphisms. Proc Natl Acad Sci USA 1989; 86:2766–2770

Oskato et al., "Ataxia-telangiectasia: allelic association with 11q22-23 markers in Moroccan-Jewish patients. 43rd Annual Meeting of the American Society of Human Genetics, New Orleans, La. (1993).

Ozelius et al., "Strong alleleic association between the torsion dystonia gene (DYT1) and loci on chromosome 9q34 in Ashkenazi Jews" *Am. J. Hum. Genet.* 50:619–628 (1992).

Parimoo et al., "cDNA selection: Efficient PCR approach for the selection of cDNAs encoded in large chromosomal DNA fragments" *Proc. Natl. Acad. Sci. USA*, 88:9623–9627 (1991).

Pease et al., "Light-generated oligonucleotide arrays for rapid DNA sequence analysis", *Proc. Natl. Acad. Sci. USA* 91(11):5022–5026 (1994)

Richard et al., *Genomics* 17, 1 (1993).

Rothstein, "Targeting, disruption, replacement, and allele rescue: integrative DNA transformation in yeast" in *Methods in Enzymology*, Vol. 194, "Guide to Yeast Genetics and Molecular Biology", eds. C. Guthrie and G. Fink, Academic Press, Inc., Chap. 19, pp. 281–301 (1991).

Rotman et al., "Three dinucleotide repeat polymorphisms at the ataxia-telangiectasia locus" *Human Molecular Genetics* (1994b).

Rotman et al., "A YAC contig spanning the ataxia-telangiectasia locus (groups A and C) on chromosome 11q22-23. *Genomics* (1994c).

Rotman et al., "Physical and genetic mapping of the ATA/ATC locus in chromosome 11q22-23" *Int. J. Radiat. Biol.* (1994d).

Rotman et al., "Rapid identification of polymorphic CA-repeats in YAC clones" *Molecular Biotechnology* (1995).

Savitsky et al., "A single gene with homologies to phosphatidylinositol 3-kinases and rad3+ is Mutated in all complementation groups of ataxia-telangiectasia" *Science*, 268:1749–1753 (Jun. 23, 1995)

Schedl et al., "A yeast artificial chromosome covering the tyrosinase gene confers copy number-dependent expression in transgenic mice", *Nature*, Vol. 362, pp. 258–261 (1993).

Sirugo et al., "Friedreich ataxia in Louisiana Acadians: Demonstration of a founder effect by analysis of microsatellite-generated extended haplotypes" *Am. J.Hum. Genet.*, 50:559–566 (1992).

Shiloh, "Ataxia-telangiectasia: closer to unraveling the mystery" *European Journal of Human Genetics* (1995)

Shiloh et al., *Am. J. Hum. Genet.* 55 (suppl.), A49 (1994)

Strauss et al., "Germ line transmission of a yeast artificial chromosome spanning the murine $\alpha_1$ . (I) collagen locus", *Science*, Vol. 259, pp. 1904–1907 (1993).

Tagle et al., "Magnetic capture of expressed sequences encoded within large genomic segments" *Nature*, 361:751–753 (1993).

The European Polycystic Kidney Disease Consortium, "The polycystic kidney disease 1 gene encodes a 14 kb transcript and lies within a duplicated region on chromosome 16" *Cell*, 77:881–894 (1994).

The Huntington's Disease Collaborative Research Group, "A novel gene containing a trinucleotide repeat that is expanded and unstable on Huntington's disease chromosomes" *Cell*, 72:971–983 (1993).

Trofatter et al., "A novel moesin-, ezrin-, radixin-like gene is a candidate for the neurofibromatosis 2 tumor suppressor" *Cell*, 72:791–800 (1993).

Vanagaite et al., "Physical localization of microsatellite markers at the ataxia-telangiectasia locus at 11q22-23. *Genomics*, 22:231–233 (1994a).

Vanagaite et al., "High-density microsatellite map of ataxia-telangiectasia locus" *Human Genetics* 95:451–453 (1995).

Vetrie et al., "The gene involved in X-linked agammaglobulinemia is a member of the src family of protein-tyrosine kinases" *Nature*, 361:226–233 (1993).

Weber and May, "Abundant class of human DNA polymorphisms which can be typed using the polymerase chain reaction" *Am. J. Hum. Genet.*, 44:388–396 (1989).

Ziv et al., "Ataxia-telangiectasia: linkage analysis in highly inbred Arab and Druze families and differentiation from an ataxia-microcephaly-cataract syndrome" *Hum. Genet.*, 88:619–626 (1992).

Ziv et al. "The ATC (ataxia-telangiectasia complementation group C) locus localizes to 11q22-q23. *Genomics*, 9:373–375 (1991).

---

We claim:

1. A purified and isolated cDNA having a sequence selected from the group consisting of SEO ID No:1, SEQ ID No:3 and SEQ ID No:9, mutations in which cause ataxia-telangiectasia.

2. A purified and isolated mRNA having a sequence complementary to said sequences of claim 1.

3. A purified and isolated cDNA having a sequence which is set forth in SEO ID No:3.

4. A purified and isolated cDNA having a sequence which is set forth in SEQ ID No:9.

5. A purified and isolated cDNA which differs from that of claim 1 due to a mutation event selected from the group consisting of point mutations, deletions, insertions and rearrangements, such that the encoded amino acid sequence is altered from that encoded by SEQ ID No: 1, 3 or 9, imparting ataxia-telangiectasia.

6. The cDNA of claim 5 wherein the mutations are as set forth in Table 1 which contains a listing of mutations which cause protein truncation and thereby ataxia-telangiectasia.

7. A vector comprising an expression control sequence operatively linked to the cDNA of claim 1.

8. A vector comprising an expression control sequence operatively linked to a cDNA as set forth in claim 5.

9. A host cell which is transformed with the vector of claim 7, wherein said host cell is selected from the group consisting of suitable eucaryotic and procaryotic cells for expressing said vector.

10. A host cell which is transformed with the vector of claim 8, wherein said host cell is selected from the group consisting of suitable eucaryotic and procaryotic cells for expressing said vector.

11. The host cell of claim 9 wherein said host cell is $E. coli$.

12. A cell line containing a cDNA of claim 1 which is operatively linked to an expression control sequence appropriate for said cell line.

13. A cell line containing a cDNA of claim 3 which is operatively linked to an expression control sequence appropriate for the cell line.

14. A cell line containing a cDNA of claim 4 which is operatively linked to an expression control sequence appropriate for said cell line.

15. A cell line containing a cDNA of claim 6 which is operatively linked to an expression control sequence appropriate for said cell line.

* * * * *